US006930114B2

(12) United States Patent
Niewöhner et al.

(10) Patent No.: US 6,930,114 B2
(45) Date of Patent: Aug. 16, 2005

(54) PYRROLO (2.1A)DIHYDROISOQUINOLINES AND THEIR USE AS PHOSPHODIESTERASE 10A INHIBITORS

(75) Inventors: Ulrich Niewöhner, deceased, late of Wermelskirchen (DE); by Maria Theresia Niewöhner, legal representative, Wermelskirchen (DE); Marcus Bauser, Wuppertal (DE); Jens-Kerim Ergüden, Wulfrath (DE); Dietmar Flubacher, Freiburg (DE); Paul Naab, Wuppertal (DE); Thorsten-Oliver Repp, Wesseling (DE); Jürgen Stoltefuss, Haan (DE); Nils Burkhardt, Dusseldorf (DE); Andrea Sewing, Broastairs (GB); Michael Schauer, Wuppertal (DE); Karl-Heinz Schlemmer, Wuppertal (DE); Olaf Weber, Wulfrath (DE); Stephen J. Boyer, Hilden (DE); Mark Miglarese, Ivorytown, CT (US)

(73) Assignee: Bayer Pharmaceuticals Corporation, West Haven, CT (US)

( * ) Notice: Subject to any disclaimer, the term of this patent is extended or adjusted under 35 U.S.C. 154(b) by 0 days.

(21) Appl. No.: 10/451,707

(22) PCT Filed: Dec. 4, 2001

(86) PCT No.: PCT/EP01/14187

§ 371 (c)(1),
(2), (4) Date: Feb. 9, 2004

(87) PCT Pub. No.: WO02/48144

PCT Pub. Date: Jun. 20, 2002

(65) Prior Publication Data

US 2004/0138249 A1 Jul. 15, 2004

Related U.S. Application Data

(60) Provisional application No. 60/310,312, filed on Aug. 6, 2001, and provisional application No. 60/255,206, filed on Dec. 13, 2000.

(51) Int. Cl.$^7$ ............... A61K 31/4745; C07D 471/04; A61P 35/00
(52) U.S. Cl. ............... 514/294; 514/287; 546/94; 546/65
(58) Field of Search ............... 546/94, 65; 514/294, 514/287

(56) References Cited

U.S. PATENT DOCUMENTS 4,694,085 A 9/1987 Losel et al. ............... 546/65
4,719,216 A 1/1988 Maryanoff ............... 514/292

FOREIGN PATENT DOCUMENTS

| EP | 0303446 | 2/1989 |
| FR | 0007348 | 10/1969 |
| GB | 1153670 | 5/1969 |
| WO | 9855118 | 12/1998 |
| WO | 0129199 | 4/2001 |

OTHER PUBLICATIONS

Strandtmann et al. J. Med. Chem. (1967), 10(6);1063–1065.*

Sofina et al. Experimental Evaluation of Antitumor Drugs in the USA and USSR and Clinical Correlations. NCI Monograph 55. NIH Publication No. 80–1933 (1980).*

Fujishige et al. 1999, J. Biol. Chem. 274(26): 18433–18445.*

Anderson, et al., "Synthesis and Antileukemic Activity of Bis[[(carbamoyl)oxy]methyl]–substituted Pyrrolo[2,1–a] isoquinolines, Pyrrolo[1,2–a]quinolines, Pyrrolo[2,1–a] isobenzazepines, and Pyrrolo[1,2–a]benzazepines", J. Med. Chem., 31(11):2097–2102 (1988).

Meyer, H., "Pyrrolo durch cyclisierende Michael–Addition von Enaminen", Liebigs Ann. Chem., pp. 1534–1544(1981).

Ambros, et al., "Synthesis and Antitumor Activity of Methoxy–indolo[2,1–a]isoquinolines", Arch. Pharm., 321: 481–486(1988).

Fujishige, et al., "Cloning and Characterization of a Novel Human Phosphodiesterase That Hydrolyzes Both cAMP and cGMP (PDE10A)", J. Biol. Chem., 274(26): 18438–18445(1999).

Lowe, et al., "Growth Factor–Induced Transcription Via The Serum Response Element Is Inhibited by Cyclic Adenosine 3',5'–Monophosphate in MCF–7 Breast Cancer Cells", Endocrinology, 138(6): 2219–2226(1997).

Albert, D., "The Effect of Cyclic–AMP on the Regulation of c–myc Expression in T Lymphoma Cells", J. Clin. Invest., 95: 1490–1496(Apr., 1995).

Mednieks, et al., "Site–selective 8–Cl–cAMP Which Causes Growth Inhibition and Differentiation Increases DNA (CRE)–binding Activity in Cancer Cells", FEBS Lett., 254(1,2): 83–88(Aug. 1989).

Fentiman, et al., "Cyclic AMP Inhibits the Growth of Human Breast Cancer Cells in Defined Medium", Mol. Biol. Med., 2: 81–88(1984).

Cassoni, et al., "Oxytocin Inhibits the Proliferation of MDA–MB231 Human Breast–Cancer Cells Via Cyclic Adenosine Monophosphate and Protein Kinase A", Int. J. Cancer, 72: 340–344(1997).

Shafer, et al., "Reduces NDA Synthesis and Cell Viability in Small Cell Lung Carcinoma by Treatment with Cyclic AMP Phosphodiesterase Inhibitors", Biochem. Pharmacol., 56: 1229–1236(1998).

(Continued)

Primary Examiner—Evelyn Mei Huang
(74) Attorney, Agent, or Firm—Susan M. Pellegrino

(57) ABSTRACT

The present invention relates to pyrrolo[2.1-a] dihydroisoquinolines which are inhibitors of phosphodiesterase 10a and can be used for combating cancer.

8 Claims, No Drawings

OTHER PUBLICATIONS

Hoosein, et al., "Promotion of Differentiation in Human Colon Carcinoma Cells by Vasoactive Intestinal Polypeptide", Regul. Peptides, 24: 15–26(1989).

Veber, et al., "Evidence for a Growth Effect of Epidermal Growth Factor on MDA–MB–231 Breast Cancer Cells", Eur. J. Cancer, 30A(9): 1352–1359(1994).

Fontana, et al., "Inhibition of Human Mammary Carcinoma Cell Proliferation by Retinoids and Intracellular cAMP–Elevating Compounds", J. Natl. Cancer Inst., 78(6): 1107–1112(Jun. 1987).

Slotkin, et al., "β–adrenoceptor Signaling and its Control of Cell Replication in MDA–MB–231 Human Breast Cancer Cells", Breast Cancer Res. And Treatment, 60: 153–166(2000).

Singer, et al., "Cyclic Nucleotide Phosphodiesterases in Neoplastic and Nonneoplastic Human Mannary Tissues", Cancer Res., 36: 60–66(Jan. 1976).

Soderling, et al., "Isolation and Characterization of a Dual–substrate Phosphodiesterase Gene Family:PDE10A", Proc. Natl. Acad. Sci., 96: 7071–7076(Jun. 1999).

Loughney, et al., "Isolation and Characterization of PDE10A, a Novel Human 3',5'–cyclic Nucleotide Phosphodiesterase", Gene, 234: 109–117(1999).

Anderson, et al., "Synthesis and Murine Antineoplastic Activity of Bis[(carbamoyloxy)methyl] Derivatives of Pyrrolo[2,1–a]isoquinoline", J. Med. Chem., 27: 1321–1325(1984).

* cited by examiner

PYRROLO (2.1A)DIHYDROISOQUINOLINES AND THEIR USE AS PHOSPHODIESTERASE 10A INHIBITORS

This application is a 371 of PCT/EP01/14187, filed Dec. 4, 2001.

The present invention relates to pyrrolo[2.1-a] dihydroisoquinolines which are inhibitors of phosphodiesterase 10a, a process for preparing those compounds and a method of treating cancer by administering those compounds.

Cyclic AMP metabolism is regulated by the opposing activities of adenylyl cyclase, which generates cAMP in response to extracellular stimuli (e.g. engagement of G-protein coupled receptors by their cognate ligands), and 3',5'-cyclic nucleotide phosphodiesterases (PDEs), which hydrolyze cAMP to 5'-AMP. Signal transduction via cAMP is associated with transcriptional events that can result in the inhibition of cellular proliferation (W. L. Lowe et al., Endocrinology 138, 2219 (1997); D. A. Albert, J. Clin. Invest. 95, 1490 (1995); M. I. Mednieks et al., FEBS Lett. 254, 83 (1989)). Indeed, elevation of intracellular cAMP concentration is growth inhibitory for several human tumor cell lines, including those derived from breast, lung and colorectal carcinomas (I. S. Fentimen et al., Mol. Biol. Med. 2, 81 (1984); P. Cassoni et al., Int. J. Cancer 72, 340 (1997); H. Shulamith et al., Biochem. Pharmacol. 56, 1229 (1998); N. M. Hoosein et al., Regul. Peptides 24, 15 (1989)). In several human breast carcinoma cell lines, increased cAMP production through stimulation of adenylate cyclase activity and/or reduction in cAMP catabolism through inhibition of phosphodiesterase activity has been shown to result in increased steady state levels of cAMP and growth inhibition (N. Veber et al., Eur. J. Cancer 30A, 1352 (1994); J. A. Fontana et al., J. Natl. Cancer Inst. 78, 1107 (1987); T. A. Slotkin et al., Breast Cancer Res. and Treatment 60, 153 (2000)). In contrast to breast tumor cell lines, normal human mammary epithelial cells are stimulated to proliferate by elevation of intracellular cAMP (I. S. Fentimen et al., Mol. Biol. Med. 2, 81 (1984)). These observations suggest that elevation of intracellular cAMP may selectively inhibit breast tumor cell proliferation. Interestingly, it has been reported that neoplastic mammary tissues have higher levels of low-Km phosphodiesterase activity compared to normal breast tissue, suggesting that tumors may gain a growth or survival advantage by keeping intracellular cAMP levels in check (A. Larks Singer et al., Cancer Res. 36, 60 (1976)).

The ICAST (inhibitor of Cyclic AMP Signal Transduction) gene encodes a specific 3',5'-cyclic nucleotide phosphodiesterase. Compared to corresponding normal tissues, ICAST mRNA is overexpressed in breast carcinoma specimens, liver metastases of colorectal carcinoma and non-small cell lung carcinomas. The ICAST cDNA was also recently cloned by other groups and named PDE 10a (K. Fujishige et al., J. Biol. Chem. 274, 18 438 (1999); S. H. Soderling et al., Proc. Natl. Acad. Sci. USA 96, 7071 (1999); K. Loughey et al., Gene 234, 109 (1999)). Published expression data for ICAST mRNA show a very limited distribution across adult human tissues, with highest levels observed in the testis, caudate nucleus and putamen (K. Fujishige et al., 1999). Increased expression of ICAST mRNA in human tumor specimens indicates that ICAST may play an important role in tumor cell growth and/or survival under conditions of elevated cAMP generation. Selective inhibition of ICAST activity in tumor cells should lead to increased cAMP concentrations and growth inhibition. The expression profile of ICAST and the published reports indicating that breast, lung and colon carcinomas are particularly sensitive to elevation of intracellular cAMP indicate that ICAST may play critical roles specifically in those tumor types. In addition to elevation of cAMP, inhibition of ICAST activity should also decrease the intracellular concentration of 5-AMP, which could limit purine pools and DNA synthesis in rapidly dividing tumor cells.

Certain pyrrolo[2.1-a]isoquinoline derivatives are known from the literature as, for example, hypotensive agents or psychotropic agents (e.g. GB-A 1,153,670; U.S. Pat. No. 4,694,085; Meyer, Liebigs Ann. Chem. 9, 1534–1544 (1981)). Pyrrolo[2.1-a]isoquinoline derivatives for the treatment of dermatologic diseases such as psoriasis are disclosed in WO 98/55118. However, the compounds disclosed in WO 98/55118 are described as having virtually no cytotoxic activity.

Pyrrolo[2.1-a]isoquinoline derivatives of formula (A) are described in J. Med. Chem. 27, 1321 (1984) and in J. Med. Chem. 31, 2097 (1988):

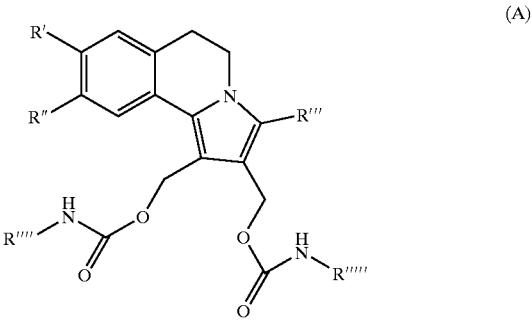

(A)

R'=H, OMe, Cl
R"=H, Cl
R'''=H, Me
R'''', R'''''=Me, Et, i-Pr, $C_6H_{11}$

These compounds are described as having antineoplastic activity, which however is stated to be due to the carbamate moieties being electrophilic centers enabling the compounds (A) to react via an alkyl-oxygen cleavage mechanism. It is not mentioned that these compounds have any PDE 10a inhibitory activity.

Tetracyclic compounds of formula (B) containing a pyrrolo[2.1-a]isoquinoline moiety are described in Arch. Pharm. 321, 481 (1988):

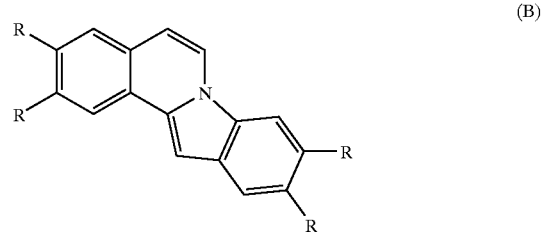

(B)

R=H, OMe

The compounds (B) are described as having anti-tumor activity due to their ability to intercalate into DNA. It is not mentioned that these compounds have any PDE 10a inhibitory activity.

Surprisingly, it has been found that the pyrrolo[2.1-a] dihydroisoquinolines of the present invention inhibit PDE 10a and exhibit an antiproliferative activity.

The present invention relates to compounds of the formula

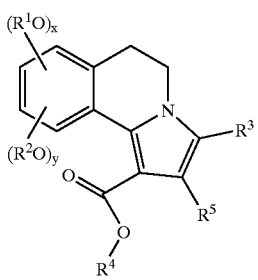

(I)

wherein
x and y independently from each other denote zero or 1 with the proviso that x+y=1 or 2;
$R^1$ and $R^2$ independently from each other denote hydrogen, $C_{1-4}$-alkyl or $CF_3$ or
$R^1$ and $R^2$ together form a $C_{1-4}$-alkylene bridge;
$R^3$ and $R^4$ independently from each other denote $C_{1-4}$-alkyl;
$R^5$ denotes $C_{6-14}$-aryl, optionally having 1 to 3 further substituents selected from the group consisting of
halogen;
$C_{1-6}$-alkyl which can be further substituted with one or more radicals selected from the group consisting of OH, halogen, $NH_2$ and $C_{1-6}$-alkoxy;
$C_{1-6}$-alkoxy which can be further substituted with one or more radicals selected from the group consisting of OH, halogen, $NH_2$, $C_{1-6}$-alkoxy and $C_{6-10}$-aryloxy;
OH;
$NO_2$;
CN;
$CF_3$;
$OCF_3$;
$NR^6R^7$;
$SR^8$;
—O—$(CH_2)_{1-4}$—O— wherein the oxygen atoms are bound to the aryl moiety in or-tho-position to each other;
phenyloxy or benzyloxy wherein the phenyl moieties optionally contain one further substituent selected from the group consisting of $C_{1-6}$-alkyl, $C_{1-6}$-alkoxy, halogen, and $NO_2$;
phenyl, optionally substituted with CN; and
4- to 9-membered aromatic heterocyclyl containing 1 to 4 hetero atoms selected from the group consisting of N, O, and S;
$R^6$ and $R^7$ independently from each other denote hydrogen, $C_{1-6}$-alkyl or, together with the nitrogen atom to which they are attached, form a 5- to 7-membered saturated, partially unsaturated or aromatic ring which can contain up to 3 further hetero atoms selected from the group consisting of N, O, and S, and which ring can contain 1 to 3 substituents selected from the group consisting of $C_{1-6}$-alkyl, $C_{1-6}$-alkoxy, $C_{6-10}$-aryl, and 4 to 9-membered aromatic heterocyclyl containing 1 to 4 hetero atoms selected from the group consisting of N, O, and S; and
$R^8$ denotes hydrogen, $C_{1-6}$-alkyl or $C_{6-10}$-aryl-$C_{1-6}$-alkyl
with the proviso that 8,9-dimethoxy-3-methyl-2-phenyl-5,6-dihydro-pyrrolo-[2.1-a]-isoquinoline-1-carboxylic acid ethyl ester is excluded,
and an isomer, a pharmaceutically acceptable) salt, a hydrate or a hydrate of a (pharmaceutically acceptable) salt thereof.

An alternative embodiment of the present invention relates to compounds of formula (I), wherein
x and y independently from each other denote zero or 1 with the proviso that x+y=1 or 2;
$R^1$ and $R^2$ independently from each other denote hydrogen, $C_{1-4}$-alkyl or $CF_3$ or
$R^1$ and $R^2$ together form a $C_{1-4}$-alkylene bridge;
$R^3$ and $R^4$ independently from each other denote $C_{1-4}$-alkyl;
$R^5$ denote (i) phenyl, optionally having 1 to 3 further substituents selected from the group consisting of
F, Cl, Br;
$C_{1-6}$-alkyl;
$C_{1-6}$-alkoxy;
$C_{6-10}$-aryloxy-$C_{1-6}$-alkoxy;
OH;
$NO_2$;
CN;
$CF_3$;
$OCF_3$;
$NR^6R^7$;
$SR^8$;
—O—$(CH_2)_{2-3}$—O— wherein the oxygen atoms are bound to the phenyl moiety in ortho-position to each other;
phenyloxy or benzyloxy wherein the phenyl moieties optionally contain one further substituent selected from the group consisting of $C_{1-6}$-alkyl, $C_{1-6}$-alkoxy, F, Cl, Br, and $NO_2$;
phenyl, optionally substituted with CN; and
benzoxazolyl;
(ii) napthyl, optionally having 1 to 3 further substituents selected from the group consisting of
F, Cl, Br;
$C_{1-6}$-alkyl;
$C_{1-6}$-alkoxy; and
$CF_3$; and
$NR^6R^7$ (wherein $R^6$ and $R^7$ are as defined above); or
(iii) phenanthrenyl;
$R^6$ and $R^7$ independently from each other denote hydrogen, $C_{1-6}$-alkyl or, together with the nitrogen atom to which they are attached, form a 5- to 7-membered saturated heterocyclyl which can contain up to 3 further hetero atoms selected from the group consisting of N, O, and S, and which saturated heterocyclyl can contain 1 to 3 substituents selected from the group consisting of $C_{1-6}$-alkyl, $C_{1-6}$-alkoxy, $C_{6-10}$-aryl and 4- to 9-membered aromatic heterocyclyl containing 1 to 4 hetero atoms selected from the group consisting of N, O, and S; and
$R^8$ denotes hydrogen, $C_{1-6}$-alkyl or $C_{6-10}$-aryl-$C_{1-6}$-alkyl
with the proviso that 8,9-dimethoxy-3-methyl-2-phenyl-5,6-dihydro-pyrrolo-[2.1-a]-isoquinoline-1-carboxylic acid ethyl ester is excluded,
and an isomer, a (pharmaceutically acceptable) salt, a hydrate or a hydrate of a (pharmaceutically acceptable) salt thereof.

A further alternative embodiment of the present invention relates to compounds of formula (I), wherein
x and y independently from each other denote zero or 1 with the proviso that x+y=1 or 2;
$R^1$ and $R^2$ independently from each other denote hydrogen, $C_{1-4}$-alkyl or $CF_3$ or
$R^1$ and $R^2$ together form a methylene bridge;
$R^3$ and $R^4$ independently from each other denote $C_{1-4}$-alkyl;

R⁵ denotes
(i) phenyl, optionally having 1 to 3 further substituents selected from the group consisting of
F, Cl, Br;
$CH_3$, $C_2H_5$, $i-C_3H_7$;
$OCH_3$, $OC_2H_5$, $i-OC_3H_7$;
phenyloxy-$C_{1-4}$-alkoxy;
OH;
$NO_2$;
CN;
$CF_3$;
$OCF_3$;
$NR^6R^7$;
$SR^8$;
—O—$(CH_2)_{2-3}$—O— wherein the oxygen atoms are bound to the phenyl moiety in ortho-position to each other;
phenyloxy or benzyloxy wherein the phenyl moieties optionally contain one further substituent selected from the group consisting of $C_{1-4}$-alkyl, $C_{1-4}$-alkoxy, F, Cl, Br, and $NO_2$;
phenyl, optionally substituted with CN; and
benzoxazolyl;
(ii) napthyl, optionally having 1 to 3 further substituents selected from the group consisting of
F, Cl, Br;
$C_{1-4}$-alkoxy;
$CF_3$; and
$NR^6R^7$ (wherein $R^6$ and $R^7$ are as defined above); or
(iii) phenanthrenyl;
$R^6$ and $R^7$ independently from each other denote hydrogen, $C_{1-6}$-alkyl or, together with the nitrogen atom to which they are attached, form a 5- to 7-membered saturated heterocyclyl; and
$R^8$ denotes hydrogen, $C_{1-4}$-alkyl or phenyl-$C_{1-4}$-alkyl
with the proviso that 8,9-dimethoxy-3-methyl-2-phenyl-5,6-dihydro-pyrrolo-[2.1-a]isoquinoline-1-carboxylic acid ethyl ester is excluded,
and an isomer, a (pharmaceutically acceptable) salt, a hydrate or a hydrate of a (pharmaceutically acceptable) salt thereof.

Compounds (I) wherein the radicals $(R^1O)_x$ and $(R^2O)_y$ are attached to the phenyl ring in the following positions, are particularly preferred:

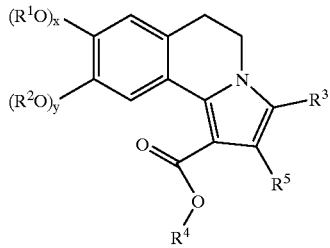

Pharmaceutically acceptable salts according to the invention are non-toxic salts which in general are accessible by reaction of the compounds (I) with an inorganic or organic base or acid conventionally used for this purpose. Non-limiting examples of pharmaceutically acceptable salts of compounds (I) include the alkali metal salts, e.g. lithium, potassium and sodium salts, the alkaline earth metal salts such as the magnesium and calcium salts, the quaternary ammonium salts such as, for example, the triethyl ammonium salts, acetates, benzene sulphonates, benzoates, dicarbonates, disulphates, ditartrates, borates, bromides, carbonates, chlorides, citrates, dihydrochlorides, fumarates, gluconates, glutamates, hexyl resorcinates, hydrobromides, hydrochlorides, hydroxynaphthoates, iodides, isothionates, lactates, laurates, malates, maleates, mandelates, mesylates, methylbromides, methylnitrates, methylsulphates, nitrates, oleates, oxalates, palmitates, pantothenates, phosphates, diphosphates, polygalacturonates, salicylates, stearates, sulphates, succinates, tartrates, tosylates, valerates, and other salts used for medicinal purposes.

The present invention includes both the individual enantiomers or diastereomers and the corresponding racemates, diastereomer mixtures and salts of the compounds according to the invention. In addition, all possible tautomeric forms of the compounds described above are included according to the present invention. The diastereomer mixtures can be separated into the individual isomers by chromatographic processes. The racemates can be resolved into the respective enantiomers either by chromatographic processes on chiral phases or by resolution.

In the context of the present invention, the substituents, if not stated otherwise, in general have the following meaning:

Alkyl per se as well as the prefixes "alkyl" and "alk" in the terms "alkylcarbonyl", "alkylsulphonyl", "alkylaminocarbonylamino", "alkoxy" and "alkoxycarbonyl" represent a linear or branched alkyl radical preferably having 1 to 12, more preferably 1 to 6 carbon atoms. Non-limiting examples of alkyl radicals include methyl, ethyl, propyl, isopropyl, butyl, isobutyl, pentyl, isopentyl, hexyl, and isohexyl.

Non-limiting examples of alkylcarbonyl radicals include acetyl, ethylcarbonyl, propylcarbonyl, isopropylcarbonyl, butylcarbonyl and isobutylcarbonyl. The terms "alkylcarbonyl" and "acyl" are used synonymously.

Non-limiting examples of alkylsulphonyl radicals include methylsulphonyl, ethylsulphonyl, propylsulphonyl, isopropylsulphonyl, butylsulphonyl and isobutylsulphonyl.

Non-limiting examples of alkylaminocarbonylamino radicals include methylaminocarbonylamino, ethylaminocarbonylamino, propylaminocarbonylamino, isopropylaminocarbonylamino, butylaminocarbonylamino and isobutylaminocarbonylamino.

Non-limiting examples of alkoxy radicals include methoxy, ethoxy, propoxy, isopropoxy, butoxy, isobutoxy, pentoxy, isopentoxy, hexoxy, isohexoxy. The terms "alkoxy" and "alkyloxy" are used synonymously.

Non-limiting examples of alkoxycarbonyl include methoxycarbonyl, ethoxycarbonyl, propyloxycarbonyl, isopropyloxycarbonyl, butyloxycarbonyl and isobutyloxycarbonyl.

. . . alkyl in the term "aryl-alkyl" represents a linear or branched (bivalent) alkylene radical preferably having 1 to 4 carbon atoms. Non-limiting examples include methylene, 1,2-ethylene, 1,2- and 1,3-propylene, and 1,2-, 1,3-, 1,4- and 2,3-butylene; methylene is preferred.

Alkylene represents a linear or branched (bivalent) alkylene radical preferably having 1 to 4 carbon atoms. Non-limiting examples of alkylene radicals include methylene, ethylene, propylene, α-methylethylene, β-methylethylene, α-ethylethylene, β-ethylethylene, butylene, α-methylpropylene, β-methylpropylene, and γ-methylpropylene.

Cycloalkyl represents a saturated cycloalkyl radical preferably having 3 to 8 carbon atoms. Non-limiting examples of cycloalkyl radicals include cyclopropyl, cyclopentyl, cyclohexyl, cycloheptyl and cyclooctyl; cyclopropyl, cyclopentyl and cyclohexyl are preferred.

Aryl per se and in the terms "aryloxy", "aryl-alkyl" and "arylaminocarbonylamino" represents an aromatic radical preferably having 6 to 14, more preferably 6 to 10 carbon atoms. Non-limiting examples of aryl radicals include phenyl, naphthyl and phenanthrenyl; non-limiting examples of aryloxy radicals include phenyloxy; non-limiting examples of aryl-alkyl radicals include benzyl; non-limiting examples of arylaminocarbonylamino radicals include phenylaminocarbonylamino, benzylaminocarbonylamino, naphthylaminocarbonylamino, and phenanthrenylaminocarbonylamino.

Heterocyclyl in the context of the invention represents a saturated, partially unsaturated or aromatic preferably 4- to 9-membered, for example 5- to 6-membered ring which can contain 1 to 4 hetero atoms from the group consisting of S, N and O which ring can be bound via a carbon atom or a nitrogen atom, if such an atom is present. Non-limiting heterocyclyl examples include oxadiazolyl, thiadiazolyl, pyrazolyl, pyridyl, pyrimidinyl, pyridazinyl, pyrazinyl, chinolinyl, isochinolinyl, indolyl, thienyl, furyl, pyrrolyl, N-methylpyrrolyl, indazolyl, benzimidazolyl, pyrrolidinyl, piperazinyl, tetrahydropyranyl, tetrahydrofuranyl, 1,2,3-triazolyl, thiazolyl, oxazolyl, imidazolyl, morpholinyl, thiomorpholinyl or piperidyl. Preferred examples include thiazolyl, furyl, oxazolyl, pyrazolyl, triazolyl, pyridyl, pyrimidinyl, pyridazinyl and tetrahydropyranyl. The terms "heteroaryl" and "hetaryl" denote an aromatic heterocyclic radical.

Halogen in the context of the invention represents fluorine, chlorine, bromine and iodine.

The present invention also relates to a process for manufacturing the compounds according to the invention comprising
the reaction of a compound of the formula

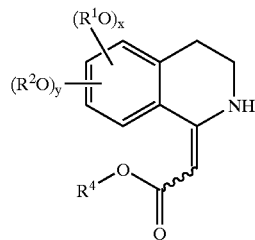

(IV)

wherein
x, y, $R^1$, $R^2$ and $R^4$ are as defined above,
[A] with compounds of the formulae (II) and (III)

wherein
$R^3$ and $R^5$ are as defined above, or
[B] with a compound of the formula (V)

wherein
$R^3$ and $R^5$ are as defined above,
and optionally
[C] the conversion of compound (I) obtained through either process [A] or [B] into an isomer, a (pharmaceutically acceptable) salt, a hydrate or a hydrate of a (pharmaceutically acceptable) salt thereof.

The compounds (II) are commercially available or can be synthesized according to methods commonly known to those skilled in the art (I. T. Harrison and S. Harrison, Compendium of Organic Synthetic Methods, Wiley-Interscience, pp. 132–176; T. D. Harris and G. P. Roth, J. Org. Chem. 44, 146 (1979); E. Müller (Ed.), "Methoden der Organischen Chemie" (Houben-Weyl), Vol. VII/1 Sauerstoff-Verbindungen II, Georg Thieme Verlag, Stuttgart 1954).

The compounds (III) are commercially available.

The compounds (IV) can be synthesized by reacting compounds of the formula (VI)

wherein
x, y, $R^1$ and $R^2$ are as defined above,
with compounds of the formula (VII)

wherein
$R^4$ is as defined above and
L is a leaving group, for example a halogen radical such as Cl, or a radical of the formula to give compounds of the formula (VIII)

wherein
x, y, $R^1$, $R^2$ and $R^4$ are as defined above,
and reacting compound (VIII) with a dehydrating agent.

The compounds (VI) are commercially available or can be synthesized according to methods commonly known to those skilled in the art (Mayer et al., Heterocycles 31, 1035 (1990); E. Müller (Ed.), "Methoden der Organischen Chemie" (Houben-Weyl), 4$^{th}$ ed., Vol. 11/1 Stickstoff-Verbindungen II, Georg Thieme Verlag, Stuttgart 1957; Shepard et al. in J. Org. Chem. 17, 568 (1952) and in J. Am. Chem. Soc. 72, 4364 (1950)).

The compounds (VII) are commercially available or can be synthesized according to methods commonly known to those skilled in the art [e.g. via acylation of acetic acid with an alkyl chloroformate or dialkyl carbonate (March, Advanced Organic Chemistry, $3^{rd}$ ed., p. 440–441, Wiley 1985) and converting the resulting monoester of malonic acid into e.g. the corresponding acid chloride or anhydride by methods commonly known to those skilled in the art (see e.g. March, Advanced Organic Chemistry, $3^{rd}$ ed., p. 355, 388, Wiley 1985)].

The reaction between the compounds (VI) and (VII) is preferably carried out in a solvent. Suitable solvents comprise the customary organic solvents which are inert under the reaction conditions. Non-limiting examples include ethers such as diethyl ether, dioxane, tetrahydrofuran, 1,2-dimethoxy ethane; hydrocarbons such as benzene, toluene, xylene, hexane, cyclohexane, mineral oil fractions; halogenated hydrocarbons such as dichloromethane, trichloromethane, carbon tetrachloride, dichloroethane, trichloroethylene, chlorobenzene; ketones such as acetone; esters such as ethyl acetate; nitriles such as acetonitrile; heteroaromatics such as pyridine; polar solvents such as dimethyl formamide or hexamethyl phosphoric acid tris-amide; and mixtures thereof. Dichloromethane is preferred.

Compound (VII) is generally employed in an amount of from 1 to 4 mol per mol of compound (VI); an equimolar amount or slight excess of compound (VII) is preferred.

The reaction between the compounds (VI) and (VII) is preferably carried out in the presence of a base. Non-limiting examples embrace alkali metal hydrides and alkali metal alkoxides such as, for example, sodium hydride and potassium tert.-butoxide; $C_{1-4}$-alkyl amines such as, for example, triethyl amine; cyclic amines such as, for example, piperidine, pyridine, dimethylamino pyridine; and—preferably—1,8-diazabicyclo[4.3.0]undec-7-ene (DBU). The base is generally employed in an amount of from 1 to 4 mol per mol of compound (VI); an equimolar amount or slight excess of the base is preferred.

The reaction of the compounds (VI) and (VII) can generally be carried out within a relatively wide temperature range. In general, the reaction is carried out within a range of from −20 to 200° C., preferably from 0 to 70° C., and more preferably at room temperature.

For the cyclization of the compounds (VIII) to yield compounds (IV), dehydrating agents such as, for example, $P_2O_5$ or $POCl_3$ are generally employed in an amount of from 1 to 10 mol, preferably from 3 to 8 mol, per mol of compound (VIII).

The cyclization reaction of the compounds (VIII) to yield the compounds (IV) is also preferably carried out in a solvent. Non-limiting examples comprise the customary organic solvents which are inert under the reaction conditions. They preferably include ethers such as diethyl ether, dioxane, tetrahydrofuran, 1,2-dimethoxy ethane; hydrocarbons such as benzene, toluene, xylene, hexane, cyclohexane, mineral oil fractions; halogenated hydrocarbons such as dichloromethane, trichloromethane, carbon tetrachloride, dichloroethane, trichloroethylene, chlorobenzene; esters such as ethyl acetate; ketones such as acetone; nitriles such as acetonitrile; heteroaromatics such as pyridine; polar solvents such as dimethyl formamide and hexamethyl phosphoric acid tris-amide; and mixtures thereof. Toluene is preferred, if the reaction is carried out with $P_2O_5$, and acetonitrile is preferred, if the reaction is carried out with $POCl_3$ (Benovsky, Stille, Tetrahedron Lett. 38, 8475–8478 (1997)).

The temperature for the cyclization reaction of compounds (VIII) is preferably within a range of from 60 to 200° C. and more preferably within a range of from 80 to 120° C.

The above process steps are generally carried out under atmospheric pressure. However, it is also possible to carry them out under superatmospheric pressure or under reduced pressure (for example, in a range of from 0.5 to 5 bar). The reaction time can generally be varied within a relatively wide range. In general, the reaction is finished after a period of from 2 to 24 hours, preferably from 6 to 12 hours.

The reaction of the compounds (IV) with either compounds (II) and (III) or with compound (V) can be carried out as a one-pot synthesis, preferably in a solvent. Suitable solvents comprise the customary organic solvents which are inert under the reaction conditions. Non-limiting examples include ethers such as diethyl ether, dioxane, tetrahydrofuran, 1,2-dimethoxy ethane; hydrocarbons such as benzene, toluene, xylene, hexane, cyclohexane, mineral oil fractions; halogenated hydrocarbons such as dichloromethane, trichloromethane, carbon tetrachloride, dichloroethane, trichloroethylene, chlorobenzene; alcohols such as methanol, ethanol, n-propanol, isopropanol; esters such as ethyl acetate; ketones such as acetone; nitrites such as acetonitrile; heteroaromatics such as pyridine; polar solvents such as dimethyl formamide and hexamethyl phosphoric acid tris-amide; and mixtures thereof. Ethanol/isopropanol (approximately 1:1 vol/vol) mixtures are preferred.

The compounds (III) are generally employed in an amount of from 1 to 3 mol per mol of compound (II); an equimolar amount or slight excess of compound (III) is particularly preferred. The compounds (IV) are generally employed in an amount of from 0.1 to 1 mol, preferably from 0.3 to 1 mol, per mol of compounds (II).

The reactions of the compounds (IV) with either compounds (II) and (III) or with compound (V) are preferably carried out in the presence of a base. Non-limiting examples include alkali metal hydrides and alkali metal alkoxides such as, for example, sodium hydride and potassium tert.-butoxide; $C_{1-4}$-alkyl amines such as, for example, triethyl amine; cyclic amines such as, for example, pyridine, dimethylamino pyridine, 1,8-diazabicyclo[4.3.0]undec-7-ene (DBU) and—preferably—piperidine. The base is generally employed in an amount of from 0.1 to 1 mol, preferably from 0.3 to 1 mol, per mol of compound (II) or compound (V), respectively.

The reactions of the compounds (IV) with either compounds (II) and (III) or with compound (V) are generally carried out within a relatively wide temperature range. In general, they are carried out in a range of from −20 to 200° C., preferably from 0 to 100° C., and more preferably from 50 to 90° C. The steps of this reaction are generally carried out under atmospheric pressure. However, it is also possible to carry them out under superatmospheric pressure or under reduced pressure (for example, in a range of from 0.5 to 5 bar). The reaction time can generally be varied within a relatively wide range. In general, the reaction is finished after a period of from 2 to 24 hours, preferably from 6 to 12 hours.

The compounds (V) are commercially available or can be synthesized in analogy to the reaction of compounds (II) and (III) described above (in the absence of compound (IV)).

The process according to the present invention can be illustrated by the following scheme:

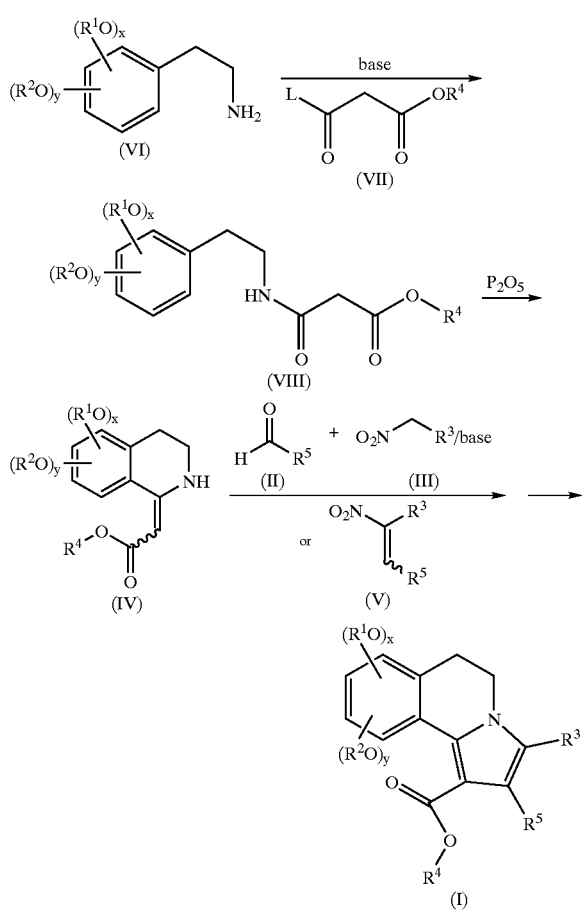

wherein x, y, $R^1$ to $R^5$, and L are as defined above.

The compounds of the present invention are inhibitors of phosphodiesterase 10a (PDE 10a). As outlined above, the inhibition of PDE 10a is a promising approach for the treatment of cancer. The biological tests described below show that the compounds according to the invention exhibit a pronounced anti-proliferation activity against tumor cells; they are therefore useful for the treatment of cancer. Furthermore, our investigations showed that they are also useful for treatment of conditions of pain and/or for the lowering of the temperature of the body in fever conditions.

The compounds according to the invention can be used as active ingredients for the production of medicaments against carcinomatous disorders. For this, they can be converted into the customary formulations such as tablets, coated tablets, aerosols, pills, granules, syrups, emulsions, suspensions and solutions using inert, non-toxic, pharmaceutically suitable excipients or solvents. Preferably, the compounds according to the invention are used in an amount such that their concentration is approximately 0.5 to approximately 90% by weight, based on the ready-to-use formulations, the concentration being dependent, inter alia, on the indication of the medicament.

The formulations can be produced, for example, by extending the active compounds with solvents and/or excipients having the above properties, where, if appropriate, additionally emulsifiers or dispersants and, in the case of water as the solvent, an organic solvent can additionally be added.

Administration can be carried out in a customary manner, preferably orally, transdermally or parenterally, for example perlingually, buccally, intravenously, nasally, rectally or inhalationally.

For human use, in the case of oral administration, it is recommended to administer doses of from 0.001 to 50 mg/kg, preferably from 0.01 to 20 mg/kg. In the case of parenteral administration such as, for example, intravenously or via mucous membranes nasally, buccally or inhalationally, it is recommended to use doses of 0.001 to 0.5 mg/kg.

If appropriate, it may be necessary to depart from the amounts mentioned above, namely depending on the body weight or the type of administration route, on the individual response towards the medicament, the manner of its formulation and the time or interval at which administration takes place. Thus, in some cases it may be sufficient to manage with less than the above mentioned minimum amount, while in other cases the upper limit mentioned must be exceeded. In the case of the administration of relatively large amounts, it may be recommended to divide these into several individual doses over the course of the day.

The compounds according to the invention are also suitable for use in veterinary medicine. For use in veterinary medicine, the compounds or their non-toxic salts can be administered in a suitable formulation in accordance with general veterinary practice. Depending on the kind of animal to be treated, the veterinary surgeon can determine the nature of use and the dosage.

The present invention provides compounds for the use in a medical application, in particular for combating cancer.

The invention further provides a method of manufacturing a pharmaceutical composition by combining at least one of the compounds of the invention with at least one pharmacologically acceptable formulating agent.

The invention further provides a pharmaceutical composition comprising as an active ingredient an effective amount of at least one of the compounds of the invention and at least one pharmacologically acceptable formulating agent.

The invention further provides a pharmaceutical composition comprising as an active ingredient an effective amount of at least one of the compounds of the invention and at least one pharmaceutical active ingredient which is different from the compounds of the invention.

The invention further provides a medicament in dosage unit form comprising an effective amount of a compound according to the invention together with an inert pharmaceutical carrier.

The invention further provides a method of combating cancer in mammals comprising the administration of an effective amount of at least one compound according to the invention either alone or in admixture with a diluent or in the form of a medicament.

The percentages in the following tests and in the Examples are—if not stated otherwise—percentages by weight; parts are parts by weight. Solvent ratios, dilution ratios and concentrations in solutions of liquids in liquids are ratios by volume.

Biological Tests

In vitro Enzyme Inhibition Assay:

Full-length recombinant PDE 10a was expressed in Sf9 insect cells (Invitrogen, Carlsbad, Calif., U.S.A.) using the Bac-to-Bac™ Baculovirus Expression System (Life Technologies, Gaithersburg, Md., U.S.A.). 48 hours post infection, cells were harvested and resuspended in 20 mL (per 1 L culture) Lysis Buffer (50 mM Tris-HCl, pH 7.4, 50 mM NaCl, 1 mM $MgCl_2$, 1.5 mM EDTA, 10% glycerol plus 20 μL Protease Inhibitor Cocktail Set III [CalBiochem, La Jolla, Calif., U.S.A.]). Cells were sonicated at 4° C. for 1 minute and centrifuged at 10,000 RPM for 30 minutes at 4° C. Supernatant was removed and stored at −20° C. for activity assays.

The test compounds were serially diluted in DMSO using two-fold dilutions to stock concentrations ranging typically from 200 μM to 1.6 μM (final concentrations in the assay range from 4 μM to 0.032 μM). 96-well assay isoplates (Wallac Inc., Atlanta, Ga., U.S.A.) were loaded with 50 μL dilution buffer per well (dilution buffer: 50 mM Tris/HCl pH 7.5, 8.3 mM $MgCl_2$, 1.7 mM EDTA, 0.2% BSA). 2 μL of the serially diluted individual test compounds were added to individual wells,m followed by 25 μL of a 1:25,000 dilution of crude recombinant PDE 10a-containing Sf9 cell lysate (diluted in dilution buffer described above). The enzymatic assay was initiated by addition of 25 μL (0.025 μCi) $^3H$ cyclic AMP tracer [5',8-$^3H$] adenosine 3',5'-cyclic phosphate (Amersham Pharmacia Biotech., Piscataway, N.J., U.S.A.) that was diluted 1:1000 in assay buffer (assay buffer: 50 mM Tris/HCl pH 7.5, 8.3 mM $MgCl_2$, 1.7 mM EDTA). Reactions were incubated at room temperature for 60 minutes and terminated by addition of 25 μL of 18 mg/mL Yttrium Scintillation Proximity Beads (Amersham Pharmacia Biotech., Piscataway, N.J., U.S.A.). Plates were sealed and incubated at room temperature for 60 minutes. Plates were read for 30 seconds/well using a Microbeta counter (Wallac Inc., Atlanta, Ga., U.S.A.). The $IC_{50}$ values were determined by plotting compound concentration versus percent inhibition. Representative results are shown in Tables 1a and 1b:

TABLE 1a

| Example (part a) No. | $IC_{50}$ (nM) |
|---|---|
| 1 | 30 |
| 6 | 56 |
| 7 | 81 |
| 8 | 46 |
| 9 | 490 |
| 10 | 42 |
| 15 | 62 |
| 25 | 96 |
| 28 | 110 |

TABLE 1b

| Example (part b) No. | $IC_{50}$ (nM) |
|---|---|
| 1 | 110 |
| 19 | 34 |
| 20 | 32 |
| 49 | 270 |

In vitro Proliferation Inhibition Assay:

MDA-MB-231 human breast carcinoma cells (ATCC # HTB26) were cultured in standard growth medium (DMEM), supplemented with 10% heat-inactivated FBS, 10 mM HEPES, 2 mM glutamine, 100 U/mL penicillin, and 100 μg/mL streptomycin) at 37° C. in 5% $CO_2$ (vol/vol) in a humidified incubator. Cells were plated at a density of 3000 cells per well in 100 μL growth medium in a 96 well culture dish. 24 hours after plating, LDH activity was determined using the Cytotox 96 Non-radioactive Cytotoxicity Kit (Promega, Madison, Wis., U.S.A.) to yield $T_{0h}$ LDH values. Briefly, cells were lysed with the addition of 200 μL of Lysis Buffer (included in the Promega Kit) and lysates were further diluted 1:50 in Lysis Buffer. 50 μL of diluted cell lysate were transferred to a fresh 96 well culture plate. The assay was initiated with the addition of 50 μL of substrate per well. Color development was allowed to proceed for 10–15 minutes. The assay was terminated with the addition of 50 μL of Stop Solution (included in Promega kit). Optical densities were determined spectrophotometrically at 490 nm in a 96 well plate reader (SpectraMax 250, Molecular Devices, Sunnyvale, Calif., U.S.A.).

Test compounds were dissolved in 100% DMSO to prepare 10 mM stocks. Stocks were further diluted 1:250 in growth medium to yield working stocks of 40 μM test compound in 0.4% DMSO. Test compounds were serially diluted in growth medium containing 0.4% DMSO to maintain constant DMSO concentrations for all wells. 50 μL of fresh growth medium and 50 μL of diluted test compound were added to each culture well to give a final volume of 200 μL. The cells with and without individual test compounds were incubated for 72 hours at which time LDH activity was measured to yield $T_{72h}$ values. Optionally, the $IC_{50}$ values can be determined with a least squares analysis program using compound concentration versus percent inhibition.

$$\% \text{ Inhibition} = [1 - (T_{72h\ test} - T_{0h})/(T_{72h\ ctrl} - T_{0h})] \times 100$$

wherein $T_{72h\ test}$=LDH activity at 72 hours in the presence of test compound, $T_{72h\ ctrl}$=LDH activity at 72 hours in the absence of test compound and $T_{0h}$=LDH activity at Time Zero Representative results are shown in Tables 2a and 2b below:

TABLE 2a

| Example (part a) No. | % inhibition at a concentration of 10 μM |
|---|---|
| 1 | 93 |
| 6 | 97 |
| 7 | 96 |
| 8 | 96 |
| 9 | 94 |
| 10 | 93 |
| 15 | 92 |
| 25 | 88 |
| 28 | 93 |

TABLE 2b

| Example (part b) No. | % inhibition at a concentration of 10 μM |
|---|---|
| 1 | 89 |
| 19 | 87 |
| 20 | 86 |
| 49 | 58 |

In vivo Tumor Growth Inhibition Assay:

Inhibition of tumor growth in vivo is readily determined via the following assay:

MDA-MB-231 cells are cultured as described above. The cells were harvested by trypsinization, washed, counted, adjusted to $2.5 \times 10^7$ cells/mL with ice-cold PBS, and subsequently stored on ice until transplantation. Xenograft experiments are conducted using eight-to-ten week-old female athymic mice with an average body mass of 20–25 g. Approximately $5 \times 10^6$ cells in a total volume of 0.2 mL PBS were injected subcutaneously in the flank region. Thereafter the mice were randomized and divided into several groups that reflect different dosages or schedules, respectively (n=10 mice/group). The test compounds were administered starting at day 1 at different dosages (e.g. 10, 20 and 40 mg/kg) and different schedules (e.g. Q1D×15, Q2D×7, Q3D×5). Test compounds were formulated for oral administration in a vehicle for oral administration composed of polyethylene glycol-400, ™Cremophor, ethanol and 0.9% saline (40:5:5:50). Tumor measurements were performed twice per week. Tumor weights are calculated using the formula $(a \times w^2)/2$. Animals were sacrificed on day 15 after transplantation and plasma was harvested for pharmacokinetic analyses.

Abbreviations used in this Specification

| | |
|---|---|
| BSA | bovine serum albumin |
| ™ Cremophor | non-ionic emulsifyer from BASF |
| DBU | 1,8-diazabicyclo[5.4.0]undec-7-ene |
| DMEM | Dulbecco's Modified Eagle Medium, Life Technologies, Gaithersburg, MD, U.S.A. |
| DMF | N,N-dimethyl formamide |
| DMSO | dimethyl sulphoxide |
| EDTA | ethylene diamine tetraacetate |
| FBS | fetal bovine serum |
| HEPES | N-(2-hydroxyethyl)-piperazine-N'-(2-ethane sulphonic acid) |
| HPLC | high pressure liquid chromatography |
| LC-MS | liquid chromatography - coupled mass spectroscopy |
| LDH | lactate dehydrogenase |
| NMR | nuclear resonance spectroscopy |
| PBS | phosphate-buffered saline |
| tlc | thin layer chromatography |
| Tris/HCl | tris(hydroxymethyl)-aminomethane hydrochloride |
| ™ Triton X-100 | tert.-octylphenoxypolyethoxyethanol |

The yield percentages of the following Examples refer to the starting component which was used in the lowest molar amount.

EXAMPLES

A. LC-MS/HPLC Methods

| Method A: | | | |
|---|---|---|---|
| MS equipment: | Micromass Quattro LCZ | | |
| | ionisation mode: | ESI positive/negative | |
| HPLC equipment: | HP 1100 | | |
| | UV detection: | 208–400 nm | |
| | temperature: | 40° C. | |
| Column: | ™ Symmetry C 18 | | |
| | 50 mm × 2.1 mm | 3.5 µm | |
| Supplier: | Waters | | |

| Gradient: | Time [min.] | A: % | B: % | Flow [mL/min.] |
|---|---|---|---|---|
| | 0.00 | 10.0 | 90.0 | 0.50 |
| | 4.00 | 90.0 | 10.0 | 0.50 |
| | 6.00 | 90.0 | 10.0 | 0.50 |
| | 6.10 | 10.0 | 90.0 | 1.00 |
| | 7.50 | 10.0 | 90.0 | 0.50 |

A: 0.1% strength solution of formic acid in acetonitrile
B: 0.1% strength aqueous formic acid

| Method B: | | | |
|---|---|---|---|
| Column: | ™ Kromasil C 18 | | |
| | 60 mm × 2.0 mm | | |

| Gradient: | Time [min.] | A: % | B: % | Flow [mL/min.] |
|---|---|---|---|---|
| | 0.00 | 90.0 | 10.0 | 0.75 |
| | 0.50 | 90.0 | 10.0 | 0.75 |
| | 4.50 | 10.0 | 90.0 | 0.75 |
| | 6.50 | 10.0 | 90.0 | 0.75 |
| | 7.50 | 90.0 | 10.0 | 0.75 |

A: 0.001% strength aqueous $H_3PO_4$
B: acetonitrile

| Method C: | | | |
|---|---|---|---|
| MS equipment: | Micromass TOF-MUX-Interface 4-fold parallel injection | | |
| | ionisation mode: | ESI positive | |
| HPLC equipment: | Waters 600 | | |
| | UV detection: | 210 nm | |
| | temperature: | 40° C. | |
| Column: | Symmetry C 18 | | |
| | 50 mm × 2.1 mm | 3.5 µm | |
| Supplier: | Waters | | |

| Gradient: | Time [min.] | A: % | B: % | Flow [mL/min.] |
|---|---|---|---|---|
| | 0.00 | 10.0 | 90.0 | 0.75 |
| | 0.50 | 10.0 | 90.0 | 0.75 |
| | 4.00 | 90.0 | 10.0 | 0.75 |
| | 5.50 | 90.0 | 10.0 | 0.75 |
| | 5.60 | 10.0 | 90.0 | 1.25 |
| | 6.50 | 10.0 | 90.0 | 0.75 |

A: 0.1% strength solution of formic acid in acetonitrile
B: 0.1% strength aqueous formic acid

| Method D: | | | |
|---|---|---|---|
| MS equipment: | Micromass Platform LCZ | | |
| | ionisation mode: | ESI positive/negative | |
| HPLC equipment: | HP 1100 | | |
| | UV detection: | 208–400 nm | |
| | temperature: | 40° C. | |
| Column: | Symmetry C 18 | | |
| | 50 mm × 2.1 mm | 3.5 µm | |
| Supplier: | Waters | | |

| Gradient: | Time [min.] | A: % | B: % | Flow [mL/min.] |
|---|---|---|---|---|
| | 0.00 | 10.0 | 90.0 | 0.50 |
| | 4.00 | 90.0 | 10.0 | 0.50 |
| | 6.00 | 90.0 | 10.0 | 0.50 |
| | 6.10 | 10.0 | 90.0 | 1.00 |
| | 7.50 | 10.0 | 90.0 | 0.50 |

A: 0.1% strength solution of formic acid in acetonitrile
B: 0.1% strength aqueous formic acid

| Method E: | |
|---|---|
| Column: | Kromasil C 18 |
| | 60 mm × 2.0 mm |

| Gradient: | Time [min.] | A: % | B: % | Flow [mL/min.] |
|---|---|---|---|---|
| | 0.00 | 98.0 | 2.0 | 0.75 |
| | 4.50 | 10.0 | 90.0 | 0.75 |
| | 6.50 | 10.0 | 90.0 | 0.75 |

-continued

| | | | |
|---|---|---|---|
| 6.70 | 98.0 | 2.0 | 0.75 |
| 7.50 | 98.0 | 2.0 | 0.75 |

A: 0.5% strength aqueous HClO₄
B: acetonitrile

B. Starting Materials
I. Phenethyl Amines

The substituted 2-phenethyl amines are commercially available or can be prepared in analogy to anyone of the following procedures, e.g. starting from the corresponding benzaldehydes (see also Shepard et al. in J. Org. Chem. 17, 568 (1952) and in J. Am. Chem. Soc. 72, 4364 (1950)).

I.1. 2-[3-(Trifluoromethoxy)-phenyl]-ethyl amine

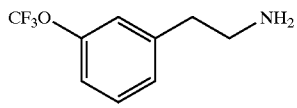

2-[3-(Trifluoromethoxy)-phenyl]-ethyl amine was obtained by hydrogenation of 3-[3-(trifluoromethoxy)-phenyl]-acetonitrile in analogy to the method described by Shepard et al. in J. Org. Chem. 17, 568 (1952) and in J. Am. Chem. Soc. 72, 4364 (1950).

I.2 2-(3-Methoxy-4-propoxyphenyl)-ethyl amine

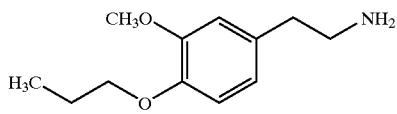

2-(3-Methoxy-4-propoxyphenyl)-ethyl amine was obtained starting from 3-methoxy-4-hydroxy-benzaldeyde, alkylation with n-propyl bromide (Dickinson et al, J. Chem. Soc. 1927, 1894) and then following the sequence described by Shepard et al. in J. Org. Chem. 17, 568 (1952) and in J. Am. Chem. Soc. 72, 4364 (1950).

II. Amides

II.1. Ethyl 3-{[2-(3,4-dimethoxyphenyl)-ethyl]-amino}-3-oxopropanoate

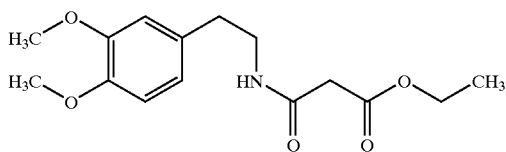

A solution of 12.4 g (82.7 mmol) of ethyl 3-chloro-3-oxopropanoate in 150 mL of dichloromethane was added at room temperature to a solution of 15.0 g (82.7 mmol) of 2-(3,4-dimethoxyphenyl)-ethyl amine and 12.6 g (82.7 mmol) of DBU in 300 ml of dichloromethane. The mixture was stirred at room temperature overnight, then water was added, and the organic layer was washed three times with water. The organic phase was dried over Na₂SO₄, and the solvent was evaporated under reduced pressure to give the title compound.

Yield: 91.3%.

¹H NMR (400 MHz, CDCl₃):

δ=1.26 (t, J=7.1 Hz, 3H), 2.78 (t, J=7.0 Hz, 2H), 3.27 (s, 2H), 3.53 (q, J=6.0 Hz, 2H), 3.86 (s, 3H), 3.88 (s, 3H), 4.16 (q, J=7.1 Hz, 2H), 6.70–6.76 (m, 2H), 6.81 (d, J=8.7 Hz, 1H), 7.12 (s, 1H).

The following amides were obtained according to an analogous procedure:

II.2. Methyl 3-{[2-(3,4-dimethoxyphenyl)-ethyl]-amino}-3-oxopropanoate

II.3. Ethyl 3-{[2-(3-methoxy-4-ethoxyphenyl)-ethyl]-amino}-3-oxopropanoate

II.4. Ethyl 3-{[2-(3-methoxy-4-propoxyphenyl)-ethyl]-amino}-3-oxopropanoate

II.5. Methyl 3-{[2-(2-methoxy-3-methoxyphenyl)-ethyl]-amino}-3-oxopropanoate

II.6. Ethyl 3-{[2-(5-methoxyphenyl)-ethyl]-amino}-3-oxopropanoate

II.7. Ethyl 3-{[2-(3-ethoxy-4-methoxyphenyl)-ethyl]-amino}-3-oxopropanoate

II.8. Ethyl 3-{[2-(3-methoxyphenyl)-ethyl]-amino}-3-oxopropanoate

II.9. Ethyl 3-{[2-(3,5-dimethoxyphenyl)-ethyl]-amino}-3-oxopropanoate

II.10. Ethyl 3-[(2-phenylethyl)-amino]-3-oxopropanoate

II.11. Ethyl 3-{[2-(1,3-benzodioxol-5-yl)-ethyl]-amino}-3-oxopropanoate

II.12. Ethyl 3-oxo-3-({2-[3-(trifluoromethoxy)-phenyl]-ethyl}-amino)-propanoate

III. (3,4-Dihydro-1(2H)-isoquinolinylidene)-ethanoates

III.1. Ethyl (6,7-dimethoxy-3,4-dihydro-1(2H)-isoquinolinylidene)-ethanoate

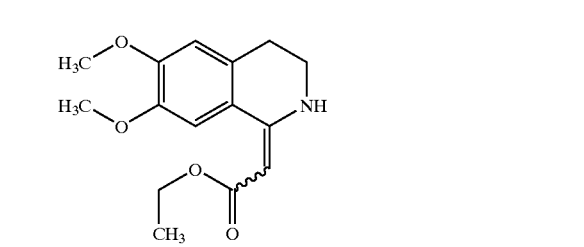

A solution of 22.0 g (74.5 mmol) of ethyl 3-{[2-(3,4-dimethoxyphenyl)-ethyl]-amino}-3-oxopropanoate Example II.1) in 400 mL of toluene was heated under reflux, and 63.4 g (446.95 mmol) of phosphorus pentoxide were added to the boiling solution in 6 portions at 15–20 min. intervals (following the course of the reaction by tlc using a cyclohexane/ethyl acetate 1:1 mixture as eluant). After cooling to room temperature, the bulk of toluene was decanted and residual toluene was removed by evaporation under reduced pressure. Solid ice was added to the residue, and the mixture was stirred at room temperature. The resulting solution was filtered and extracted several times with ethyl acetate. The combined organic phases were dried over Na₂SO₄, filtered through a pad of silica gel, and finally the solvent was evaporated under reduced pressure to give the title compound.

Yield: 87.1%.

¹H NMR (200 MHz, CDCl₃):

δ=1.30 (t, J=7.2 Hz, 3H), 2.83 (t, J=6.4 Hz, 2H), 3.32–3.52 (m, 2H), 3.89 (s, 3H), 3.91 (s, 3H), 4.17 (q, J=7.1 Hz, 2H), 5.05 (s, 1H), 6.66 (s, 1H), 7.12 (s, 1H), 9.04 (s, 1H).

The following (3,4-dihydro-1(2H)-isoquinolinylidene)-ethanoates were obtained according to an analogous procedure:

III.2 Methyl (2E,Z)-(6,7-dimethoxy-3,4-dihydro-1(2H)-isoquinolinylidene)ethanoate III.3 Ethyl (2E,Z)-(7-ethoxy-6-methoxy-3,4-dihydro-1(2H)-isoquinolinylidene)ethanoate III.4 Ethyl (2E,Z)-(6-ethoxy-7-methoxy-3,4-dihydro-1(2H)-isoquinolinylidene)ethanoate III.5 Ethyl (2E,Z)-(7-butoxy-6-methoxy-3,4-dihydro-1(2H)-isoquinolinylidene)ethanoate III.6 Methyl (2E,Z)-(5,6-dimethoxy-3,4-dihydro-1(2H)-isoquinolinylidene)ethanoate III.7 Methyl (2E,Z)-[6-(trifluoromethoxy)-3,4-dihydro-1(2H)-isoquinolinylidene]ethanoate III.8 Ethyl (2E,Z)-(6,8-dimethoxy-3,4-dihydro-1(2H)-isoquinolinylidene)-ethanoate III.9 Ethyl (2E,Z)-(3,4-dihydro-1(2H)-isoquinolinylidene)-ethanoate III.10 Ethyl (2E,Z)-7,8-dihydro[1,3]dioxolo[4,5-g]isoquinolin-5(6H)-ylideneethanoate III.11 Ethyl (2E,Z)-(6-methoxy-3,4-dihydro-1(2H)-isoquinolinylidene)-ethanoate (A) and ethyl (2E,Z)-(8-methoxy-3,4-dihydro-1(2H)-isoquinolinylidene)-ethanoate (B):

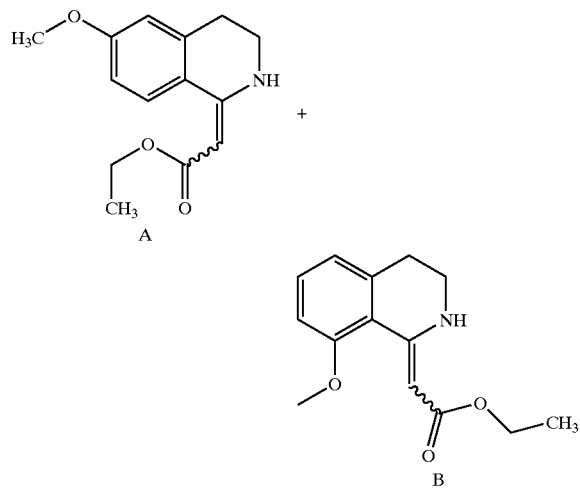

A solution of 44.10 g (170 mmol) of ethyl 3-{[2-(3-methoxyphenyl)-ethyl]-amino}3-oxopropanoate (prepared as described in II.8 from 3-methoxy-phenylethyl amine and ethyl 3-chloro-3-oxoproanoate with 95.8% yield) in 432 mL of toluene was heated under reflux, and 179.31 g (1260 mmol) of phosphorus pentoxide were added to the boiling solution in 6 portions at 15–20 min. intervals (following the course of the reaction by tlc using a cyclohexane/ethyl acetate 1:1 mixture as eluant). After cooling to room temperature, 1 L of water was added slowly with ice cooling, then the resulting mixture was made alcaline by adding potassium carbonate. The mixture was extracted 4 times with ether, the combined organic phases were dried over $Na_2SO_4$, filtered, and the solvent was evaporated. Compounds A and B were separated by silica gel chromatography: 20.5 g (48.89%) of compound A and 620 mg (1.51%) of compound B were obtained.

C. Preparation Examples

Part a

Example 1

Ethyl 2-(4-hydroxy-3,5-dimethylphenyl)-8,9-dimethoxy-3-methyl-5,6-dihydro-pyrrolo[2,1-a]isoquinoline-1-carboxylate

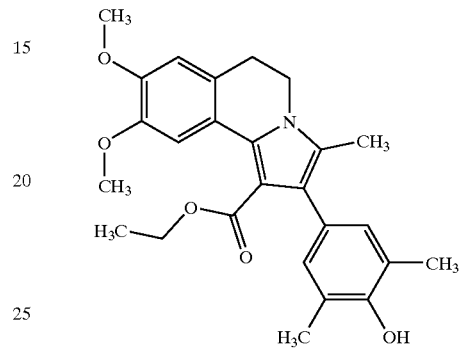

A mixture of 500 mg (1.8 mmol) of ethyl (6,7-dimethoxy-3,4-dihydro-1(2H)-isoquinolinylidene)-ethanoate (Example III.1), 558 mg (3.61 mmol) of 3,5-dimethyl-4-hydroxybenzaldehyde, 281 mg (3.61 mmol) of nitroethane and 61.4 mg (0.72 mmol) of piperidine in 10 mL of an ethanol/isopropanol 1:1 mixture was stirred at 80° C. overnight. 40 mL of isopropanol were added, the mixture was cooled to 0° C., and the resulting precipitate was filtered off. The solid was washed with ethanol and dried in vacuo to give the title compound as a white solid which was readily recrystallized from ethyl acetate to furnish white needles.

Yield: 673 mg.

$^1$H NMR (200 MHz, $CDCl_3$):

δ=0.96 (t, J=7.2 Hz, 3H), 2.17 (s, 3H), 2.21 (s, 6H), 2.98 (t, J=6.4 Hz, 2H), 3.77–3.98 (m, 2H), 3.90 (s, 3H), 3.91 (s, 3H), 4.06 (q, J=7.2 Hz, 2H), 4.56 (s, 1H), 6.71 (s, 1H), 6.88 (s, 2H), 7.88 (s, 1H).

The following Preparation Examples (Nos. 2–25) were prepared in analogy to Example 1:

| Ex. No. | Structure | Analytical data |
|---|---|---|
| 2 | ![structure] | Melting point [° C.]: 127–129 |

-continued

| Ex. No. | Structure | Analytical data |
|---|---|---|
| 3 | (structure: ethyl ester of dimethoxy-dihydropyrrolo-isoquinoline with 3-methyl and 2-(3,5-dichloro-4-aminophenyl) substituents) | $^1$H-NMR(300 MHz, DMSO-d$_6$):<br>δ = 0.97(t, J=7.2 Hz, 3H), 2.12(s, 3H),<br>2.94(t, J=6.4 Hz, 2H), 3.72(s, 3H),<br>3.79(s, 3H), 3.92(t, J=6.6 Hz, 2H),<br>4.02(q, J=7.2 Hz, 2H), 5.39(s, 2H),<br>6.93(s, 1H), 7.02(s, 2H), 7.66(s, 1H)<br>MS: 475[M + H]$^+$<br>HPLC retention time [min.]: 4.78(method A) |
| 4 | (structure: ethyl ester of dimethoxy-dihydropyrrolo-isoquinoline with 3-methyl and 2-(4-hydroxy-1-naphthyl) substituents) | MS: 458[M + H]$^+$<br>HPLC retention time [min.]: 4.42(method A) |
| 5 | (structure: ethyl ester of dimethoxy-dihydropyrrolo-isoquinoline with 3-ethyl and 2-(4-hydroxy-1-naphthyl) substituents) | MS: 472[M + H]$^+$<br>HPLC retention time [min.]: 4.57(method A) |
| 6 | (structure: methyl ester of dimethoxy-dihydropyrrolo-isoquinoline with 3-methyl and 2-(3-chloro-4-hydroxyphenyl) substituents) | Melting point [° C.]: 202–204 |

-continued

| Ex. No. | Structure | Analytical data |
|---|---|---|
| 7 | 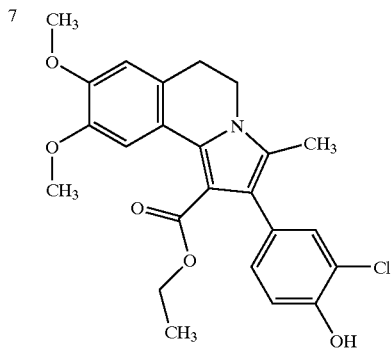 | $^1$H-NMR(300 MHz, DMSO-d$_6$):<br>δ = 0.93(t, J=7.2 Hz, 3H), 2.11(s, 3H),<br>2.94(t, J=6.4 Hz, 2H), 3.72(s, 3H),<br>3.79(s, 3H), 3.92(t, J=6.6 Hz, 2H),<br>3.99(q, J=7.2 Hz, 2H), 6.89–7.99(m, 3H),<br>7.09(s, 1H), 7.66(s, 1H), 9.95(s, 1H)<br>MS: 442[M + H]$^+$<br>HPLC retention time [min.]: 4.25(method A) |
| 8 | 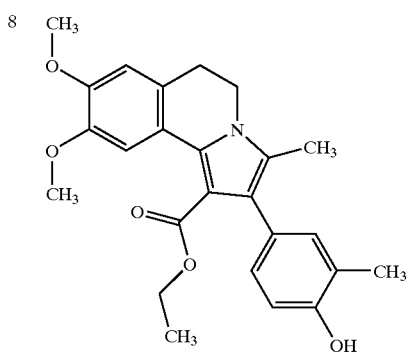 | $^1$H-NMR(300 MHz, DMSO-d$_6$):<br>δ = 0.92(t, J=7.2 Hz, 3H), 2.11(s,3H),<br>2.12(s, 3H), 2.94(t, J=6.4 Hz, 2H), 3.71(s, 3H),<br>3.78(s, 3H), 3.91(t, J=6.6 Hz, 2H),<br>3.97(q, J=7.2 Hz, 2H), 6.70–6.95(m, 4H),<br>7.60(s, 1H), 9.08(s, 1H)<br>MS: 422[M + H]$^+$<br>HPLC retention time [min.]: 4.49(method B) |
| 9 | 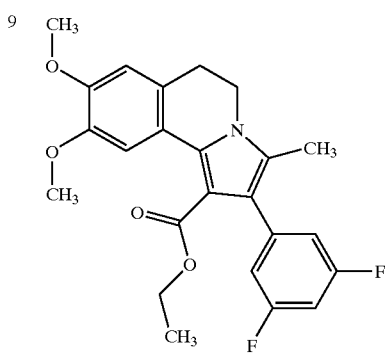 | MS: 428[M + H]$^+$<br>HPLC retention time [min.]: 4.88(method A) |
| 10 | 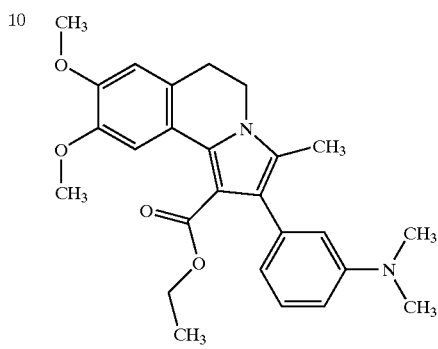 | $^1$H-NMR(300 MHz, DMSO-d$_6$):<br>δ = 0.90(t, J=7.0 Hz, 3H), 2.16(s, 3H),<br>2.88(s, 6H), 2.95(t, J=6.4 Hz, 2H), 3.72(s, 3H),<br>3.79(s, 3H), 3.89–4.03(m, 4H),<br>6.44–6.53(m, 2H), 6.60–6.67(m, 1H),<br>6.94(s, 1H), 7.15(t, J=8.1 Hz, 1H), 7.60(s, 1H)<br>MS: 435[M + H]$^+$<br>HPLC retention time [min.]: 4.07(method C) |

| Ex. No. | Structure | Analytical data |
|---|---|---|
| 11 | 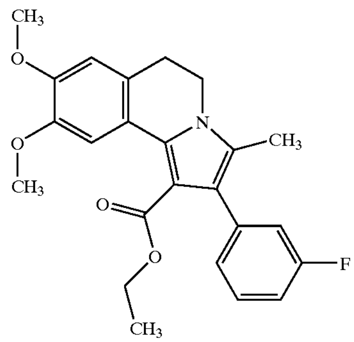 | ¹H-NMR(300 MHz, DMSO-d₆):<br>δ = 0.88(t, J=7.0 Hz, 3H), 2.14(s, 3H),<br>2.96(t, J=6.4 Hz, 2H), 3.73(s, 3H), 3.79(s, 3H),<br>3.88–4.03(m, 4H), 6.91–7.14(m, 4H),<br>7.33–7.44(m, 1H), 7.72(s, 1H)<br>MS: 410[M + H]⁺<br>HPLC retention time [min.]: 5.15(method C) |
| 12 | 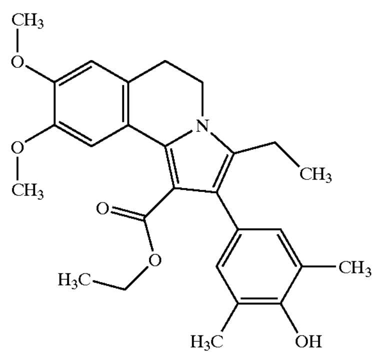 | Melting point [° C.]: 192–193 |
| 13 | 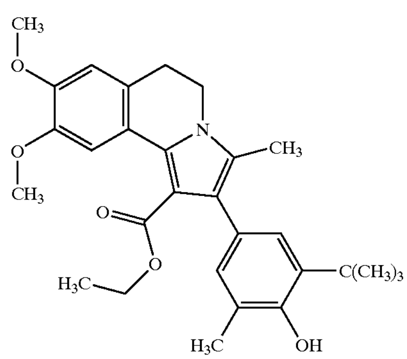 | ¹H-NMR(300 MHz, DMSO-d₆):<br>δ = 0.91(t, J=7.2 Hz, 3H), 1.36(s, 9H),<br>2.14(s, 3H), 2.19(s, 3H), 2.94(t, J=6.4 Hz, 2H),<br>3.71(s, 3H), 3.78(s, 3H), 3.87–4.01(m, 4H),<br>6.78(d, J=1.7 Hz, 1H), 6.81(d, J=1.9 Hz, 1H),<br>6.93(s, 1H), 7.57(s, 1H), 7.92(s, 1H)<br>MS: 478[M + H]⁺<br>HPLC retention time [min.]: 5.28(method C |
| 14 | 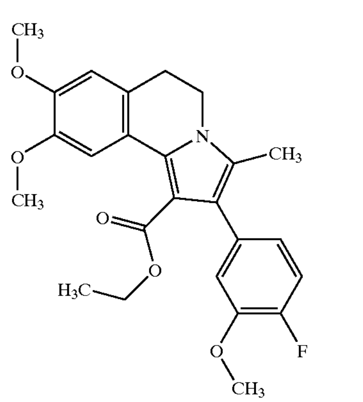 | Melting point [° C.]: 152–153 |

| Ex. No. | Structure | Analytical data |
|---|---|---|
| 15 | (structure) | Melting point [° C.]: 225–226 |
| 16 | (structure) | ¹H-NMR(400 MHz, CDCl₃):<br>δ = 0.97(t, J=7.1 Hz, 3H), 2.18(s, 3H),<br>2.82–3.07(m, 8H), 3.74–3.97(m, 8H),<br>4.07(q, J=7.1 Hz, 2H), 6.60–6.85(m, 3H),<br>7.16(d, J=8.1 Hz, 2H), 7.87(s, 1H)<br>MS: 435[M + H]⁺<br>HPLC retention time [min.]: 3.68(method B) |
| 17 | (structure) | ¹H-NMR(300 MHz, DMSO-d₆):<br>δ = 0.92(t, J=7.1 Hz, 3H), 1.32(t, J=6.8 Hz, 3H),<br>2.13(s, 3H), 2.87–3.00(m, 2H), 3.71(s, 3H),<br>3.78(s, 3H), 3.86–4.05(m, 6H),<br>6.56(d, J=7.8 Hz, 1H), 6.68(s, 1H),<br>6.76(d, J=8.1 Hz, 1H), 6.93(s, 1H), 7.59(s, 1H)<br>MS: 452[M + H]⁺<br>HPLC retention time [min.]: 4.20(method A) |
| 18 | (structure) | Melting point [° C.]: 96–97 |

-continued
| Ex. No. | Structure | Analytical data |
|---|---|---|
| 19 | 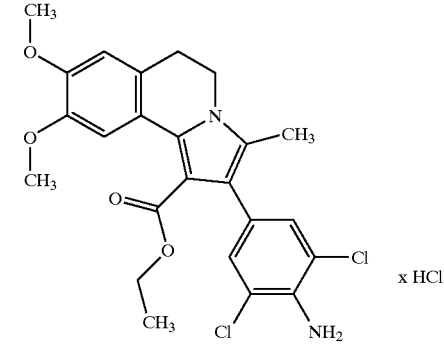 x HCl | Melting point [° C.]: 163–164 |
| 20 | 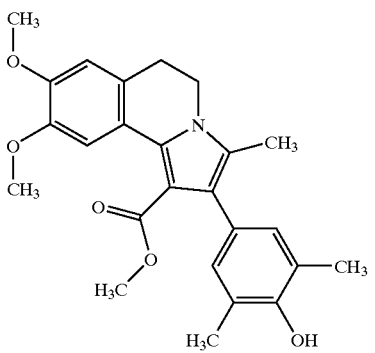 | Melting point [° C.]: 193–194 |
| 21 | 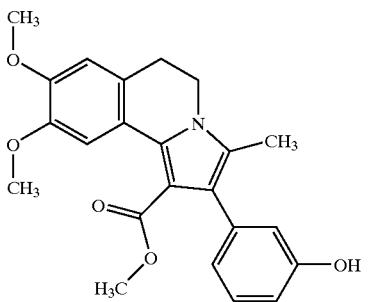 | Melting point [° C.]: 201–203 |
| 22 | 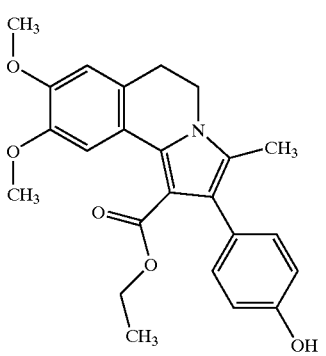 | $^1$H-NMR(300 MHz, CDCl$_3$):<br>δ = 0.95(t, J=7.2 Hz, 3H), 2.15(s, 3H),<br>2.98(t, J=6.6 Hz, 2H), 3.82–3.97(m, 2H),<br>3.90(s, 3H), 3.91(s, 3H), 4.04(q, J=7.2 Hz, 2H),<br>4.66(s, 1H), 6.71(s, 1H), 6.83(d, J=8.7 Hz, 2H),<br>7.13(d, J=9.0 Hz, 2H), 7.92(s, 1H)<br>MS: 408[M + H]$^+$<br>HPLC retention time [min.]: 4.30(method B) |

-continued

| Ex. No. | Structure | Analytical data |
|---|---|---|
| 23 | 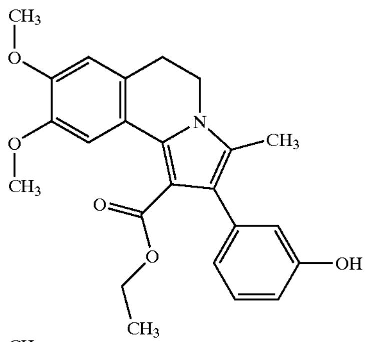 | $^1$H-NMR(300 MHz, DMSO-$d_6$): <br> δ = 0.90(t, J=7.0 Hz, 3H), 2.14(s, 3H), <br> 2.95(t, J=6.2 Hz, 2H), 3.72(s, 3H), 3.79(s, 3H), <br> 3.89–4.03(m, 4H), 6.53–6.68(m, 3H), <br> 6.94(s, 1H), 7.12(t, J=8.1 Hz, 1H), 7.63(s, 1H), <br> 9.21(s, 1H) <br> MS: 408[M + H]$^+$ <br> HPLC retention time [min.]: 4.49(method C) |
| 24 | 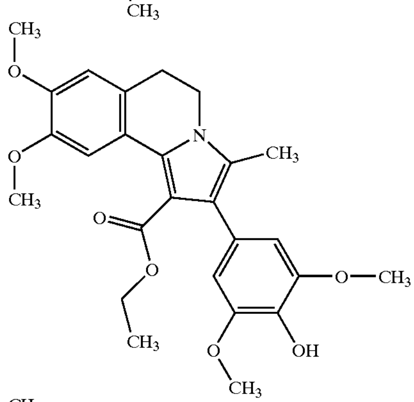 | HPLC retention time [min.]: 3.98(method A) |
| 25 | 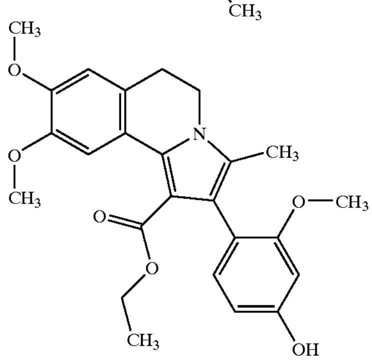 | Melting point [° C.]: 212 |

Examples 26 and 27
Ethyl 8-methoxy-9-hydroxy-2-(3,5-dimethyl-4-hydroxyphenyl)-3-methyl-5,6-dihydro[2,1-a]isoquinoline-1-carboxylate (Example 26) and
Ethyl 9-methoxy-8-hydroxy-2-(3,5-dimethyl-4-hydroxyphenyl)-3-methyl-5,6-dihydropyrrolo[2,1-a]isoquinoline-1-carboxylate (Example 27)

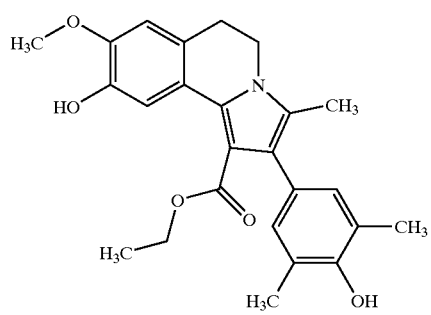

Example 26

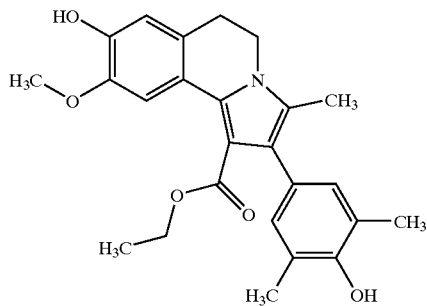

Example 27

1 g (2.3 mmol) of ethyl 2-(4hydroxy-3,5-dimethylphenyl)-8,9-dimethoxy-3-methyl-5,6-dihydropyrrolo[2,1-a]isoquinoline-1-carboxylate (Example 1) was intimately mixed with 4 g of pyridine hydrochloride and heated to fusion at 150° C. The mixture was stirred at 150° C. for 20 min., then cooled to room temperature and dissolved in a mixture of ethyl acetate and dilute hydrochloric acid. The layers were separated, the aqueous layer was extracted with ethyl acetate, and the combined organic phases were washed with water, dried over Na$_2$SO$_4$, and the solvent was evaporated under reduced pressure. Column chromatography on silica gel using a dichloromethane/ethyl acetate 10:1 mixture as eluant afforded the title compounds ethyl 8-methoxy-9-hydroxy-2-(3,5-dimethyl-4-hydroxyphenyl)-3-methyl-5,6-dihydro-pyrrolo[2,1-a]isoquinoline-1-carboxylate (Example 26):

Yield: 46 mg.

Melting point [° C.]: 218–220;

and ethyl 9-methoxy-8-hydroxy-2-(3,5-dimethyl-4-hydroxyphenyl)-3-methyl-5,6-dihydro-pyrrolo[2,1-a]isoquinoline-1-carboxylate (Example 27):

Yield: 34 mg.

Melting point [° C.]: 164–165.

Example 28

Ethyl 2-(3-aminophenyl)-8,9-dimethoxy-3-methyl-5,6-dihydropyrrolo[2,1-a]-isoquinoline-1-carboxylate

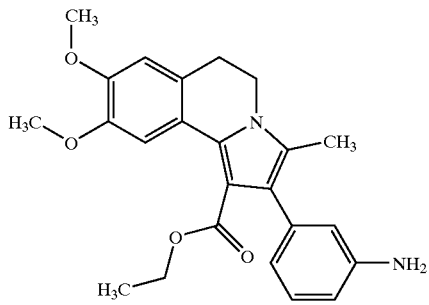

4.5 g (10.31 mmol) of ethyl 8,9-dimethoxy-3-methyl-2-(3-nitrophenyl)-5,6-dihydropyrrolo[2,1-a]isoquinoline-1-carboxylate (Example 2) were dissolved in 500 mL of warm methanol, 2.03 g of 10% strength palladium on charcoal were added, and the compound was hydrogenated at atmospheric pressure. The reaction mixture was filtered through a filter aid, the filtrate was evaporated under reduced pressure to a volume of approx. 150 mL, and the resulting precipitate was filtered off to give the title compound.

Yield: 3.36 g (80.2%).

Melting point [° C.]: 170–172.

Example 29

Ethyl 8,9-dimethoxy-3-methyl-2-(3-piperidinylphenyl)-5,6-dihydro-pyrrolo[2,1-a]-isoquinoline-1-carboxylate

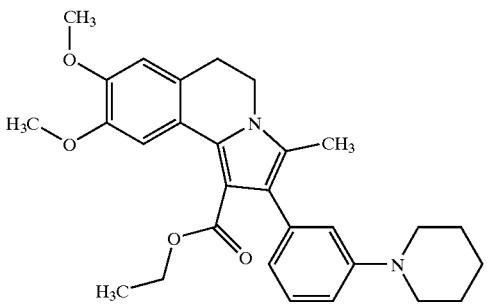

168.5 mg (1.11 mmol) of DBU and 84.9 mg (0.37 mmol) of 1,5-dibromopentane were added to a solution of 150 mg (0.37 mmol) of ethyl 2-(3-aminophenyl)-8,9-dimethoxy-3-methyl-5,6-dihydropyrrolo[2,1-a]isoquinoline-1-carboxylate (Example 28) in 3 mL of DMF. The mixture was stirred at 120° C. for 20 hours, then evaporated under reduced pressure, and the residue was taken up in an ethyl acetate/water mixture. The layers were separated, the aqueous layer was extracted with ethyl acetate, and the combined organic phases were washed with water, dried over Na$_2$SO$_4$, and the solvent was evaporated under reduced pressure. Chromatography on a short silica gel column using a dichloromethane/ethyl acetate 10:1 mixture as eluant, followed by crystallization from diethyl ether gave the title compound.

Yield: 65.2 mg.

Melting point [° C.]: 128–130.

Part b

Example 1

Ethyl 2-(3,5-dihydroxyphenyl)-8,9-dimethoxy-3-methyl-5,6-dihydro-pyrrolo[2,1-a]-isoquinoline-1-carboxylate

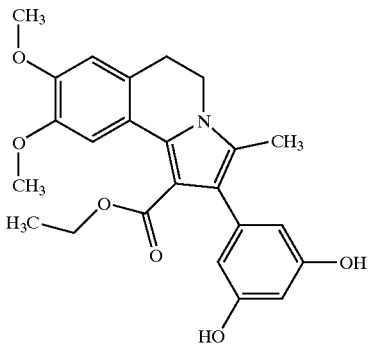

A mixture of 500 mg (1.8 mmol) of ethyl (6,7-dimethoxy-3,4-dihydro-1(2H)-isoquinolinylidene)-ethanoate (Example III.1), 499 mg (3.61 mmol) of 3,5-dihydroxybenzaldehyde, 281 mg (3.61 mmol) of nitroethane and 61.4 mg (0.72 mmol) of piperidine in 10 mL of an ethanol/isopropanol 1:1 mixture was stirred at 80° C. overnight. 40 mL of isopropanol were added, the mixture was cooled to 0° C., and the resulting precipitate was filtered off. The solid was washed with ethanol and dried in vacuo to give the title compound as a white solid which was readily recrystallized from ethyl acetate to furnish white needles.

Yield: 12.9%.

$^1$H NMR (300 MHz, DMSO-$d_6$):

δ=0.96 (t, J=7.2 Hz, 3H), 2.14 (s, 3H), 2.94 (t, J=6.6 Hz, 2H), 3.71 (s, 3H), 3.78 (s, 3H), 3.92 (t, J=6.6 Hz, 2H), 4.00 (q, J=7.2 Hz, 2H), 6.03 (d, J=2.3 Hz, 2H), 6.09 (t, J=2.3 Hz, 1H), 6.93 (s, 1H), 7.58 (s, 1H), 9.02 (s, 2H).

MS: 424.2 [M+H]$^+$

HPLC retention time [min]: 4.06 (method C)

The following Preparation Examples (Nos. 2–91) were prepared in analogy to Example 1. All aldehydes are commercially available or are prepared in analogy to published procedures (I. T. Harrison and S. Harrison, Compendium of Organic Synthetic Methods, pages 132–177, Wiley-Interscience, John Wiley & Sons, Inc.). If nitropropane is used instead of nitroethane, ethyl 3-ethyl-5,6-dihydro-pyrrolo[2,1-a]isoquinolines are obtained.

| Ex. | Structure | Analytical data |
|---|---|---|
| 2 | 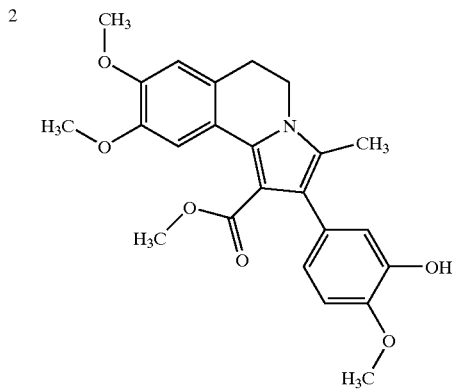 | $^1$H-NMR(300 MHz, DMSO-$d_6$):<br>δ = 2.13(s, 3H), 2.94(t, 2H), 3.54(s, 3H),<br>3.72(s, 3H), 3.77(s, 6H), 3.78(s, 3H), 3.92(t, 2H),<br>6.51–6.57(m, 1H), 6.61(d, 1H), 6.88(d, 1H),<br>6.94(s, 1H), 7.44(s, 1H), 8.86(s, 1H)<br>Melting point [° C.]: 186–187 |
| 3 | 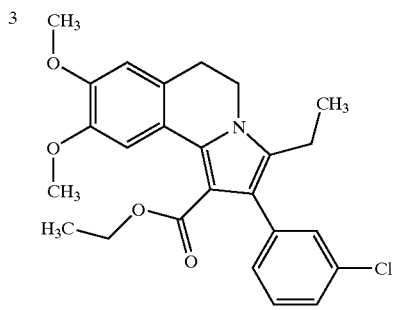 | $^1$H-NMR(200 MHz, CDCl$_3$):<br>δ = 0.91(t, J=7.1 Hz, 3H), 1.11(t, J=7.5 Hz, 3H),<br>2.52(q, J=7.3 Hz, 2H), 2.99(t, J=6.3 Hz, 2H),<br>3.82–4.09(m, 10H), 6.72(s, 1H),<br>6.96–7.46(m, 4H), 7.97(s, 1H)<br>MS: 440.1[M + H]$^+$<br>HPLC retention time [min]: 5.66(method B) |
| 4 | 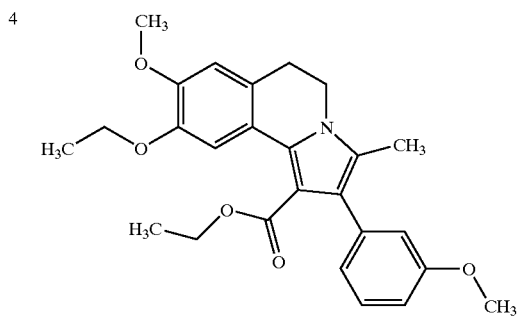 | Melting point [° C.]: 136–137<br>MS: 436.1[M + H]$^+$<br>HPLC retention time [min]: 5.2(method B) |

| Ex. | Structure | Analytical data |
|---|---|---|
| 5 | 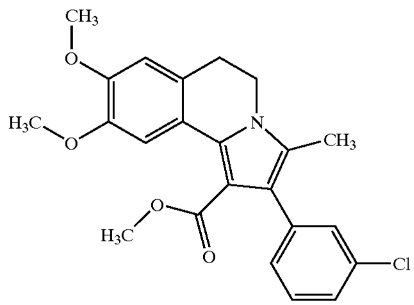 | ¹H-NMR(300 MHz, CDCl₃):<br>δ = 2.17(s, 3H), 3.00(t, 2H), 3.58(s, 3H),<br>3.90–3.94(m, hidden 2H), 3.91(s, 3H),<br>3.92(s, 3H), 6.73(s, 1H), 7.10–7.16(m, 1H),<br>7.18–7.33(m, 3H), 7.89(s, 1H) |
| 6 | 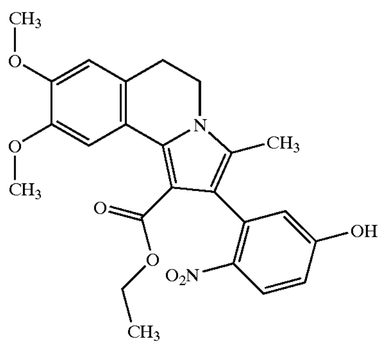 | MS: 451.3[M − H]⁺<br>HPLC retention time [min]: 4.02(method A) |
| 7 | 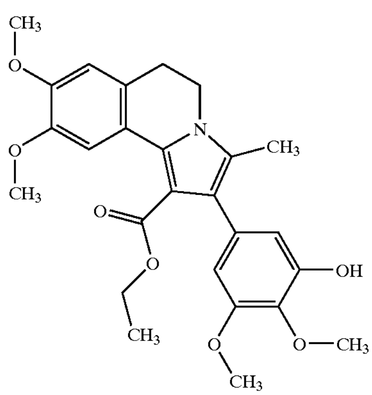 | MS: 468.2[M + H]⁺<br>HPLC retention time [min]: 4.49(method C) |
| 8 | 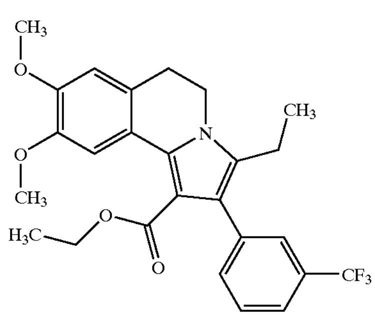 | ¹H-NMR(200 MHz, CDCl₃):<br>δ = 0.83(t, J=7.2 Hz, 3H), 1.11(t, J=7.5 Hz, 3H),<br>2.52(q, J=7.6 Hz, 2H), 3.00(t, J=6.6 Hz, 2H),<br>3.86–4.07(m, 4H), 3.91(s, 3H), 3.92(s, 3H),<br>6.73(s, 1H), 7.35–7.61(m, 4H), 8.00(s, 1H)<br>MS: 474.2[M + H]⁺<br>HPLC retention time [min]: 5.7(method B) |

-continued

| Ex. | Structure | Analytical data |
|---|---|---|
| 9 | 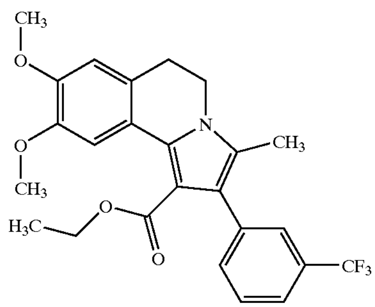 | ¹H-NMR(200 MHz, CDCl₃):<br>δ = 0.85(t, J=7.2 Hz, 3H), 2.16(s, 3H),<br>3.00(t, J=6.6 Hz, 2H), 3.84–4.07(m, 4H),<br>3.91(s, 3H), 3.93(s, 3H), 6.73(s, 1H),<br>7.36–7.61(m, 4H), 8.05(s, 1H)<br>MS: 460.1[M + H]⁺<br>HPLC retention time [min]: 5.52(method B) |
| 10 | 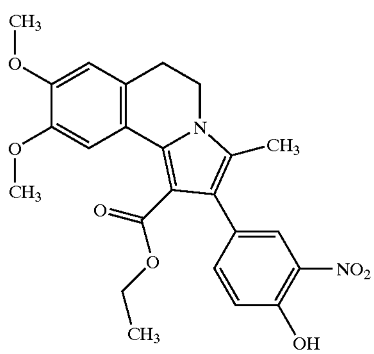 | ¹H-NMR(300 MHz, DMSO-d₆):<br>δ = 0.92(t, J=7.0 Hz, 3H), 2.13(s, 3H),<br>2.95(t, J=6.2 Hz, 2H), 3.73(s, 3H),<br>3.79(s, 3H), 3.88–4.06(m, 4H), 6.94(s, 1H),<br>7.11(d, J=8.5 Hz, 1H), 7.36(dd, J=8.5 Hz,<br>J=2.3 Hz, 1H), 7.64(d, J=2.1 Hz, 1H),<br>7.72(s, 1H), 10.81(bs, 1H)<br>MS: 453.3[M + H]⁺<br>HPLC retention time [min]: 5(method C) |
| 11 | 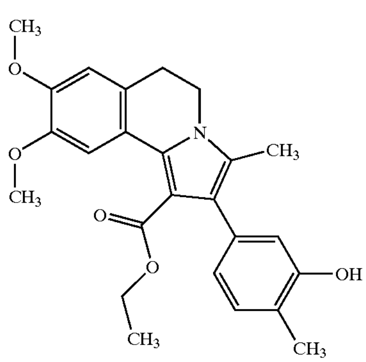 | ¹H-NMR(200 MHz, DMSO-d₆):<br>δ = 0.92(t, J=7.1 Hz, 3H), 2.12(s, 3H),<br>2.13(s, 3H), 2.95(t, J=6.2 Hz, 2H), 3.71(s, 3H),<br>3.78(s, 3H), 3.85–4.06(m, 4H),<br>6.50(d, J=7.5 Hz, 1H), 6.60(s, 1H), 6.94(s, 1H),<br>7.00(d, J=7.7 Hz, 1H), 7.57(s, 1H), 9.13(s, 1H)<br>MS: 422.0[M + H]⁺<br>HPLC retention time [min]: 4.32(method D) |
| 12 | 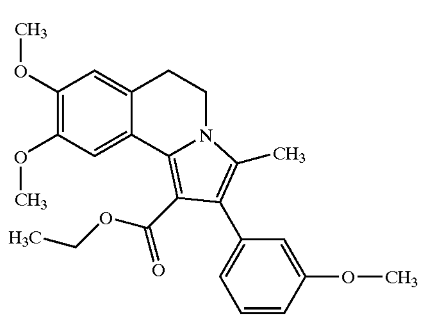 | MS: 422.1[M + H]⁺<br>HPLC retention time [min]: 5.01(method B) |

-continued

| Ex. | Structure | Analytical data |
|---|---|---|
| 13 | 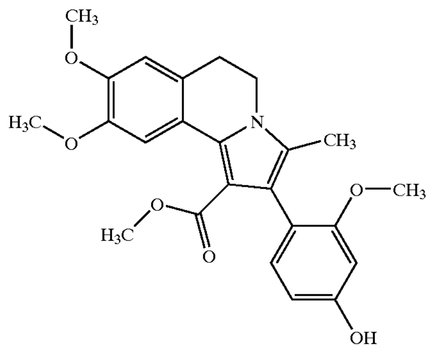 | ¹H-NMR(200 MHz, DMSO-d₆):<br>δ = 2.04(s, 3H), 2.93(t, 2H), 3.46(s, 3H),<br>3.58(s, 3H), 3.72(s, 3H), 3.78(s, 3H), 3.91(t, 2H),<br>6.29–6.41(m, 1H), 6.38(s, 1H), 6.83(d, 1H),<br>6.93(s, 1H), 7.62(s, 1H), 9.31(br s, 1H)<br>Melting point [° C.]: 252–254 |
| 14 | 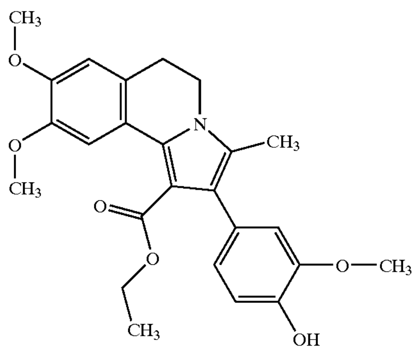 | ¹H-NMR(300 MHz, DMSO-d₆):<br>δ = 0.92(t, J=7.2 Hz, 3H), 2.13(s, 3H),<br>2.86–3.00(m, 2H), 3.72(s, 3H), 3.73(s, 3H),<br>3.78(s, 3H), 3.85–4.07(m, 4H),<br>6.57(dd, J=8.0 Hz, J=1.8 Hz, 1H),<br>6.70(d, J=1.7 Hz, 1H), 6.75(d, J=8.1 Hz, 1H),<br>6.94(s, 1H), 7.60(s, 1H), 8.83(s, 1H)<br>MS: 438.2[M + H]⁺<br>HPLC retention time [min]: 4.01(method A) |
| 15 | 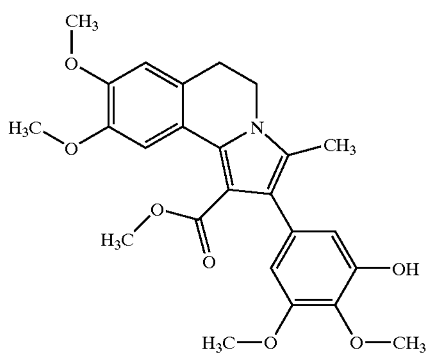 | ¹H-NMR(300 MHz, DMSO-d₆):<br>δ = 2.17(s, 3H), 2.94(t, 2H), 3.56(s, 3H),<br>3.69(s, 3H), 3.72(s, 3H), 3.79(s, 3H),<br>3.92(t, 2H), 6.23–6.31(m, 2H), 6.94(s, 1H),<br>7.44(s, 1H), 9.06(s, 1H)<br>Melting point [° C.]: 215–216 |
| 16 | 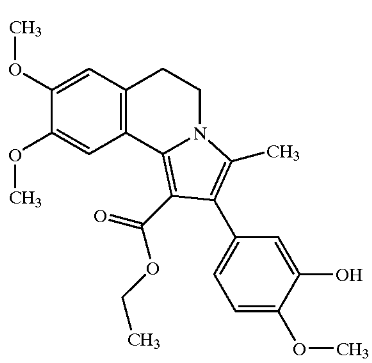 | MS: 438.2[M + H]⁺<br>HPLC retention time [min.]: 5.53(method C) |

-continued

| Ex. | Structure | Analytical data |
|---|---|---|
| 17 | [structure] | MS: 444.2[M + H]+<br>HPLC retention time [min.]: 4.91(method A) |
| 18 | [structure] | $^1$H-NMR(300 MHz, DMSO-$d_6$):<br>δ = 2.16(s, 3H), 2.96(t, 2H), 3.49(s, 3H),<br>3.74(s, 3H), 3.80(s, 3H), 3.96(t, 2H), 6.96(s, 1H),<br>7.45–7.52(m, 2H), 7.58–7.64(m, 2H), 7.62(s, 1H)<br>Melting point [° C.]: 140–141 |
| 19 | [structure] | $^1$H-NMR(200 MHz, DMSO-$d_6$):<br>δ = 2.13(s, 3H), 2.16(s, 6H), 2.99(t, 2H),<br>3.50(s, 3H), 3.73(s, 3H), 3.82(s, 3H), 3.90(t, 2H),<br>6.70(s, 2H), 6.95(d, 1H), 7.43(d, 1H), 8.09(s, 1H)<br>Melting point [° C.]: 196–198 |
| 20 | [structure] | $^1$H-NMR(300 MHz, DMSO-$d_6$):<br>δ = 0.95(t, 3H), 2.12(s, 3H), 2.99(t, 2H),<br>3.78(s, 3H), 3.87(s, 3H), 3.94(t, 2H), 3.99(q, 2H),<br>6.80–6.85(m, 1H), 6.89–6.92(m, 1H),<br>7.07–7.16(m, 2H), 7.20(s, 1H), 7.38(d, 2H)<br>Melting point [° C.]: 182–183 |

-continued
| Ex. | Structure | Analytical data |
|---|---|---|
| 21 | 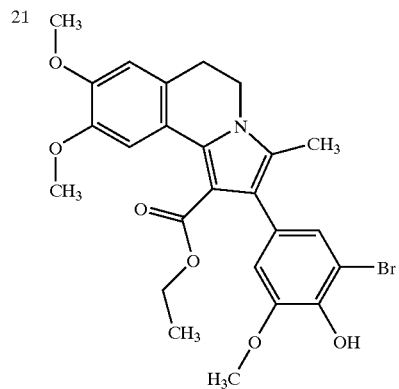 | MS: 518.2[M + H]$^+$<br>HPLC retention time [min.]: 4.45(method D) |
| 22 | 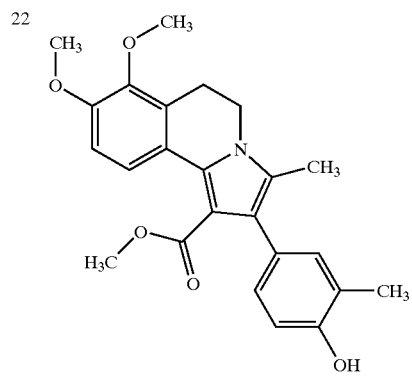 | $^1$H-NMR(200 MHz, DMSO-d$_6$):<br>δ = 2.12(s, 6H), 2.99(t, 2H), 3.50(s, 3H),<br>3.73(s, 3H), 3.82(s, 3H), 3.90(t, 2H), 6.69–<br>6.82(m, 2H), 6.85(s, 1H), 6.95(d, 1H),<br>7.44(d, 1H), 9.15(s, 1H)<br>Melting point [° C.]: 183–185 |
| 23 | 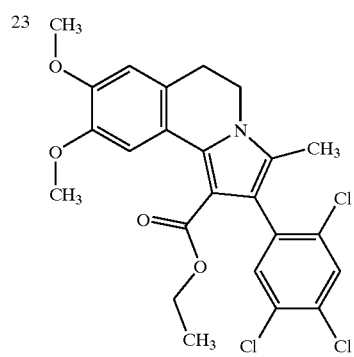 | MS: 496.1[M + H]$^+$<br>HPLC retention time [min.]: 5.39(method A) |
| 24 | 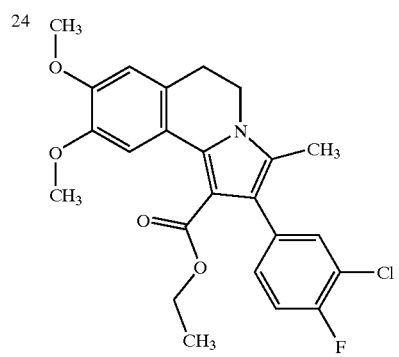 | $^1$H-NMR(200 MHz, DMSO-d$_6$):<br>δ = 0.90(t, J=7.1 Hz, 3H), 2.12(s, 3H),<br>2.95(t, J=6.2 Hz, 2H), 3.73(s, 3H),<br>3.79(s, 3H), 3.86–4.08(m, 4H), 6.95(s, 1H),<br>7.09–7.26(m, 1H), 7.30–7.47(m, 2H), 7.75(s, 1H)<br>MS: 444.2[M + H]$^+$<br>HPLC retention time [min.]: 5.03(method A) |

-continued

| Ex. | Structure | Analytical data |
|---|---|---|
| 25 | 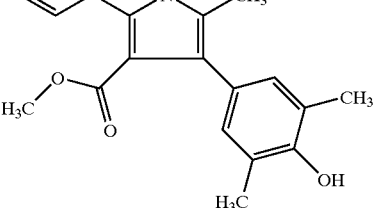 | ¹H-NMR(200 MHz, DMSO-d$_6$):<br>δ = 2.14(s, 3H), 2.16(s, 6H), 3.07(t, 2H), 3.53(s, 3H), 3.98(t, 2H), 6.71(s, 2H), 7.24(d, 1H), 7.35(br s, 1H), 7.75(d, 1H), 8.13(s, 1H)<br>Melting point [° C.]: 167–169 |
| 26 | 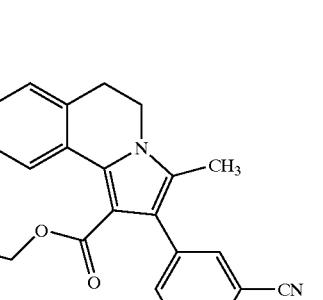 | ¹H-NMR(300 MHz, CDCl$_3$):<br>δ = 0.91(t, J=7.2 Hz, 3H), 2.14(s, 3H), 3.00(t, J=6.6 Hz, 2H), 3.84–3.97(m, 2H), 3.91(s, 3H), 3.92(s, 3H), 4.03(q, J=7.0 Hz, 2H), 6.73(s, 1H), 7.42–7.52(m, 2H), 7.53–7.60(m, 2H), 8.02(m, 1H)<br>MS: 417[M + H]$^+$, 434[M + NH$_4$]$^+$<br>HPLC retention time [min.]: 4.87(method B) |
| 27 | 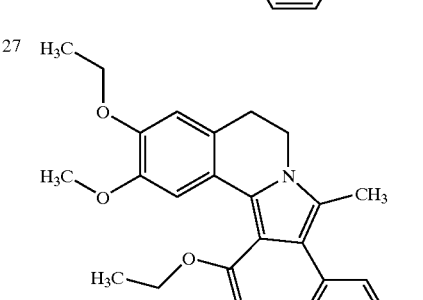 | ¹H-NMR(200 MHz, CDCl$_3$):<br>δ = 0.92(t, 3H), 1.48(t, 3H), 2.16(s, 3H), 2.98(t, 2H), 3.90(s, 3H), 3.93(t, 2H), 4.04(q, 2H), 4.16(q, 2H), 6.72(s, 1H), 7.10–7.17(m, 1H), 7.21–7.30(m, 1H), 7.98(m, 1H)<br>Melting point [° C.]: 137–138 |
| 28 | 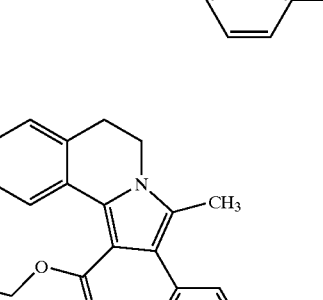 | ¹H-NMR(400 MHz, CDCl$_3$):<br>δ = 0.92(t, J=7.1 Hz, 3H), 2.16(s, 3H), 2.99(t, J=6.5 Hz, 2H), 3.86–3.96(m, 2H), 3.91(s, 3H), 3.92(s, 3H), 4.04(q, J=7.1 Hz, 2H), 6.7(s, 1H), 7.09–7.16(m, 1H), 7.21–7.31(m, 3H), 8.01(s, 1H)<br>MS: 426.2[M + H]$^+$, 443.1[M + NH$_4$]$^+$<br>HPLC retention time [min.]: 5.47(method B) |
| 29 | 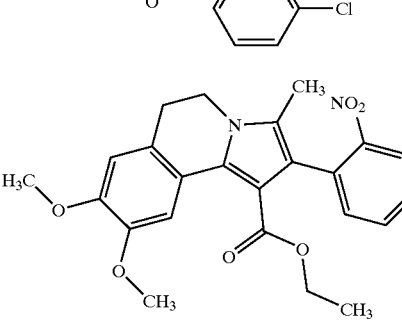 | Melting point [° C.]: 142–143 |

-continued

| Ex. | Structure | Analytical data |
|---|---|---|
| 30 | 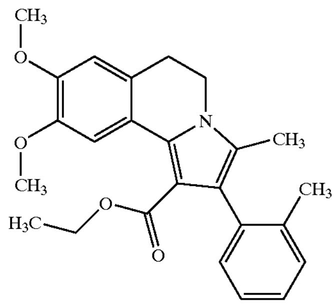 | $^1$H-NMR(200 MHz, DMSO-d$_6$):<br>δ = 0.70(t, J=7.1 Hz, 3H), 1.95(s, 3H),<br>2.01(s, 3H), 2.97(t, J=6.4 Hz, 2H),<br>3.61–4.12(m, 4H), 3.72(s, 3H), 3.79(s, 3H),<br>6.88–7.29(m, 4H), 6.95(s, 1H), 7.89(s, 1H)<br>MS: 406.3[M + H]$^+$, 423.3[M + NH$_4$]$^+$<br>HPLC retention time [min.]: 5.4(method B) |
| 31 | 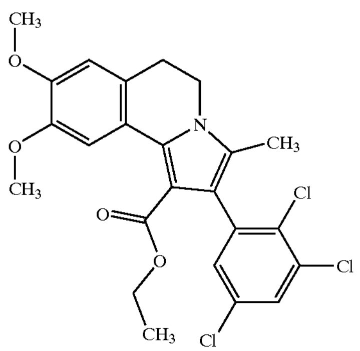 | $^1$H-NMR(200 MHz, DMSO-d$_6$):<br>δ = 0.80(t, 7.2 Hz, 3H), 2.04(s, 3H),<br>2.89–3.05(m, 2H), 3.68–4.07(m, 4H),<br>3.74(s, 3H), 3.80(s, 3H), 6.96(s, 1H),<br>7.35(d, J=2.4 Hz, 1H), 7.81(d, J=2.5 Hz, 1H),<br>8.03(s, 1H)<br>MS: 496.1[M + H]$^+$<br>HPLC retention time [min.]: 5.39 (method A) |
| 32 | 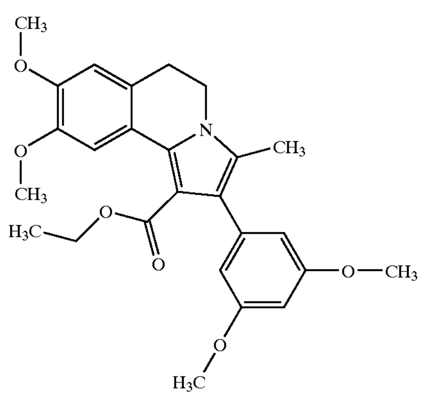 | $^1$H-NMR(300 MHz, DMSO-d$_6$):<br>δ = 0.92(t, J=7.1 Hz, 3H), 2.16(s, 3H),<br>2.95(t, J=6.2 Hz, 2H), 3.73(s, 9H),<br>3.79(s, 3H), 3.85–4.08(m, 4H),<br>6.26–6.34(m, 2H), 6.37–6.43(m, 1H),<br>6.94(s, 1H), 7.63(s, 1H)<br>MS: 452.0[M + H]$^+$<br>HPLC retention time [min.]: 4.94(method B) |
| 33 | 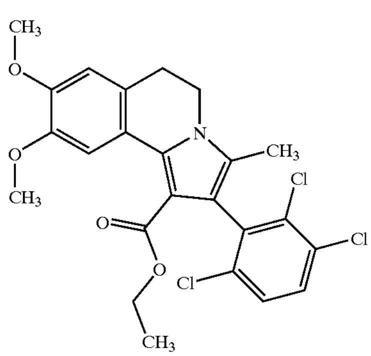 | MS: 496.1[M + H]$^+$<br>HPLC retention time [min.]: 5.12(method A) |

-continued

| Ex. | Structure | Analytical data |
|---|---|---|
| 34 | 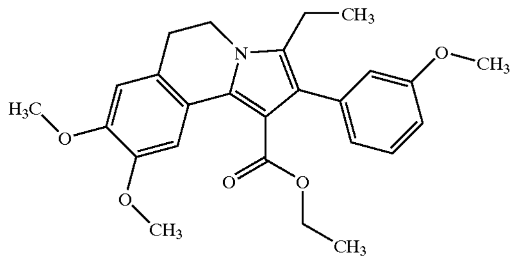 | Melting point [° C.]: 127–129 |
| 35 | 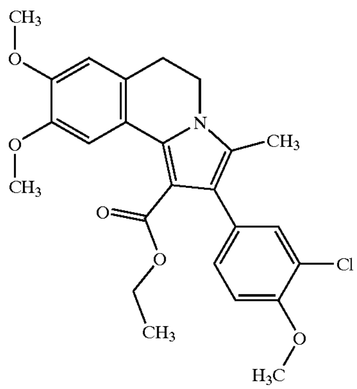 | ¹H-NMR(300 MHz, DMSO-d₆): δ = 0.93(t, J=7.2 Hz, 3H), 2.12(s, 3H), 2.95(t, J=6.4 Hz, 2H), 3.72(s, 3H), 3.79(s, 3H), 3.87(s, 3H), 3.93(t, J=6.4 Hz, 2H), 3.99(q, J=7.2 Hz, 2H), 6.94(s, 1H), 7.06–7.21(m, 3H), 7.68(s, 1H) MS: 456.2[M + H]⁺ HPLC retention time [min.]: 4.79(method A) |
| 36 | 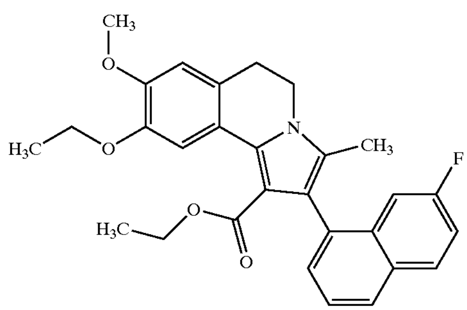 | MS: 474.4[M + H]⁺, 491.2[M + NH₄]⁺ HPLC retention time [min.]: 5.7(method B) |
| 37 | 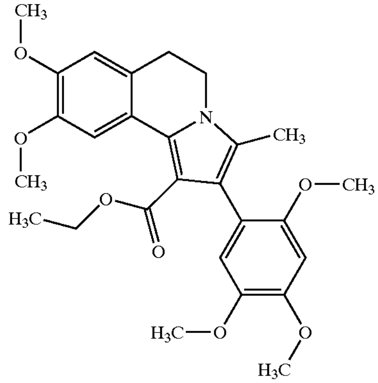 | ¹H-NMR(200 MHz, CDCl₃): δ = 0.94(t, J=7.2 Hz, 3H), 2.15(s, 3H), 3.68–4.12(m, 2H), 3.74(s, 3H), 3.83(s, 3H), 3.90(s, 3H), 3.91(s, 3H), 3.94(s, 3H), 6.58(s, 1H), 6.70(s, 1H), 6.75(s, 1H), 8.00(s, 1H) MS: 482.1[M + H]⁺ HPLC retention time [min.]: 4.5(method B) |

| Ex. | Structure | Analytical data |
|---|---|---|
| 38 | 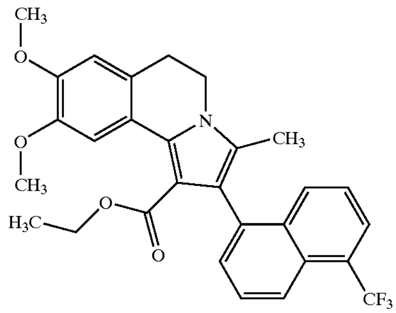 | ¹H-NMR(200 MHz, DMSO-d₆):<br>δ = 0.20(t, J=7.2 Hz, 3H), 2.00(s, 3H),<br>3.03(t, J=6.2 Hz, 2H), 3.56(q, J=7.2 Hz, 2H),<br>3.73(s, 3H), 3.81(s, 3H), 4.04(t, J=6.3 Hz, 2H),<br>6.99(s, 1H), 7.46(d, J=6.9 Hz, 1H),<br>7.56(t, J=7.7 Hz, 1H), 7.75(t, J=7.2 Hz, 1H),<br>7.90–8.13(m, 4H)<br>MS: 510.2[M + H]⁺, 527.1[M + NH₄]⁺<br>HPLC retention time [min.]: 4.49(method B) |
| 39 | 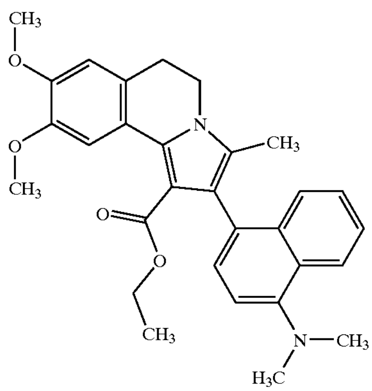 | ¹H-NMR(200 MHz, DMSO-d₆):<br>δ = 0.24(t, J=7.1 Hz, 3H), 1.99(s, 3H),<br>2.84(s, 6H), 3.01(t, J=6.3 Hz, 2H),<br>3.47–3.66(m, 2H), 3.72(s, 3H), 3.81(s, 3H),<br>4.01(t, J=6.3 Hz, 2H), 6.97(s, 1H),<br>7.12(d, J=7.7 Hz, 1H), 7.19(d, J=7.6 Hz, 1H),<br>7.31–7.51(m, 2H), 7.60(d, J=8.3 Hz, 1H),<br>7.92(s, 1H), 8.18(d, J=7.8 Hz, 1H)<br>MS: 485.0[M + H]⁺<br>HPLC retention time [min.]: 4.36(method B) |
| 40 | 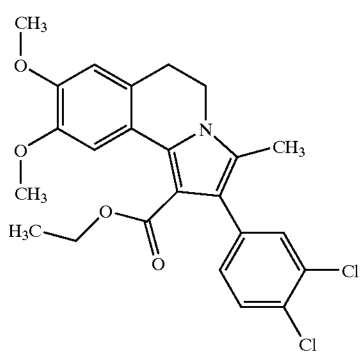 | MS: 460.2[M + H]⁺, 477.3[M + NH₄]⁺<br>HPLC retention time [min.]: 5.94(method B) |
| 41 | 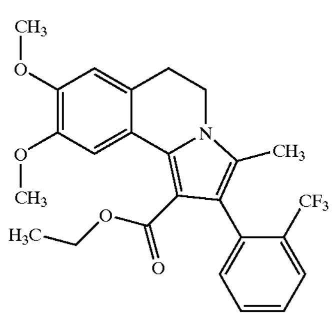 | MS: 460.3[M + H]⁺<br>HPLC retention time [min.]: 5.03(method D) |

-continued

| Ex. | Structure | Analytical data |
|---|---|---|
| 42 | (structure) | $^1$H-NMR(200 MHz, DMSO-d$_6$):<br>δ = 0.36(t, J=7.1 Hz, 3H), 1.86(s, 3H),<br>3.02(t, J=6.1 Hz, 2H), 3.52–3.86(m, 2H),<br>3.72(s, 3H), 3.77(s, 3H), 3.81(s, 3H),<br>4.01(t, J=6.2 Hz, 2H), 6.97(s, 1H),<br>7.21–7.37(m, 2H), 7.38–7.52(m, 2H),<br>7.78–7.99(m, 2H)<br>MS: 472.2[M + H]$^+$<br>HPLC retention time [min.]: 3.6(method B) |
| 43 | (structure) | $^1$H-NMR(200 MHz, DMSO-d$_6$):<br>δ = 0.91(t, 3H), 2.12(s, 3H), 2.95(t, 2H),<br>3.72(s, 3H), 3.79(s, 3H), 3.85(s, 3H), 3.93(t, 2H),<br>4.98(q, 2H), 6.88–7.04(m, 3H), 7.14(t, 1H),<br>7.67(s, 1H)<br>Melting point [° C.]: 144–145 |
| 44 | (structure) | $^1$H-NMR(200 MHz, CDCl$_3$):<br>δ = 0.97(t, J=7.1 Hz, 3H), 2.16(s, 3H),<br>2.99(t, J=6.4 Hz, 2H), 3.81–3.99(m, 2H),<br>3.91(s, 3H), 3.92(s, 3H), 4.07(q, J=7.1 Hz, 2H),<br>6.72(s, 1H), 7.09(dd, J=8.2 Hz, J=2.0 Hz, 1H),<br>7.37(d, J=2.0 Hz, 1H), 7.42(d, J=8.2 Hz, 1H),<br>7.98(s, 1H)<br>MS: 460.0[M + H]$^+$, 477.2[M + NH$_4$]$^+$<br>HPLC retention time [min.]: 5.79(method B) |
| 45 | (structure) | MS: 426.3[M + H]$^+$<br>HPLC retention time [min.]: 4.93(method D) |

| Ex. | Structure | Analytical data |
|---|---|---|
| 46 | 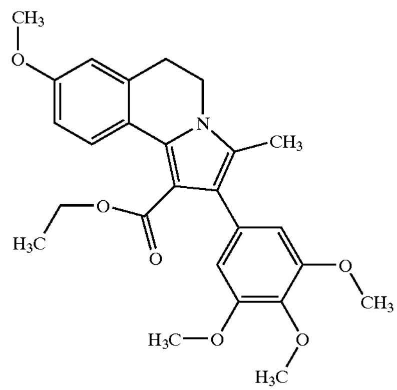 | $^1$H-NMR(300 MHz, DMSO-d$_6$):<br>δ = 0.93(t, 3H), 2.17(s, 3H), 2.99(t, 2H), 3.68(s, 3H), 3.75(s, 6H), 3.78(s, 3H), 3.94(t, 2H), 4.00(q, 2H), 6.45(s, 2H), 6.80–6.85(m, 1H), 6.89–6.92(m, 1H), 7.80(d, 1H)<br>Melting point [° C.]: 141–142 |
| 47 | 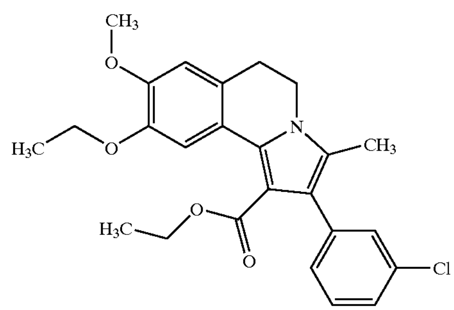 | $^1$H-NMR(200 MHz, CDCl$_3$):<br>δ = 0.92(t, 3H), 1.48(t, 3H), 2.17(s, 3H), 2.98(t, 2H), 3.91(s, 3H), 3.93(t, 2H), 4.04(q, 2H), 4.13(q, 2H), 6.72(s, 1H), 6.89–7.06(m, 3H), 7.22–7.30(m, 1H), 7.97(m, 1H)<br>Melting point [° C.]: 131–132 |
| 48 | 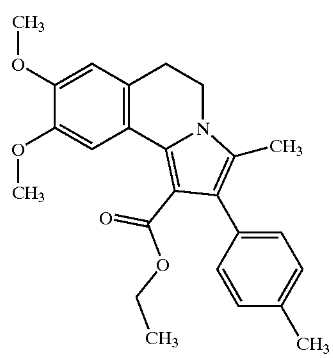 | MS: 406.3[M + H]$^+$<br>HPLC retention time [min.]: 5.03(method D) |
| 49 | 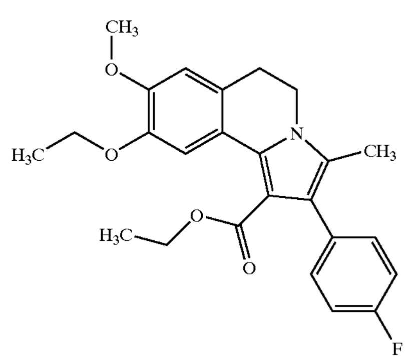 | MS: 424.1[M + H]$^+$, 441[M + NH$_4$]$^+$<br>HPLC retention time [min.]: 5.3(method B)<br>Melting point [° C.]: 143–144 |

-continued

| Ex. | Structure | Analytical data |
|---|---|---|
| 50 | 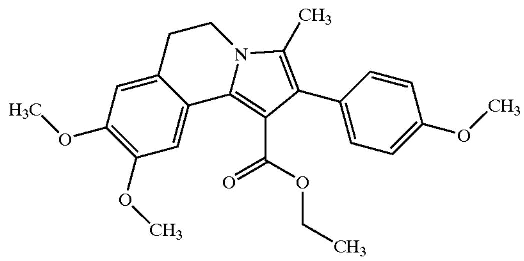 | Melting point [° C.]: 157–159 |
| 51 | 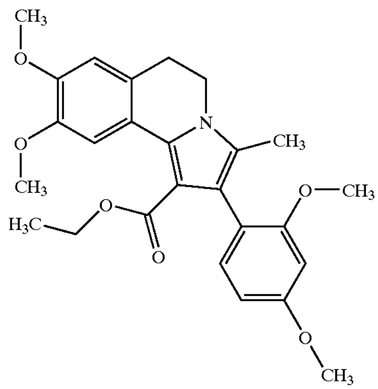 | ¹H-NMR(200 MHz, CDCl₃):<br>δ = 0.93(t, J=7.1 Hz, 3H), 2.14(s, 3H),<br>2.98(t, J=5.8 Hz, 2H), 3.70–4.11(m, 4H),<br>3.74(s, 3H), 3.85(s, 3H), 3.90(s, 3H),<br>3.91(s, 3H), 6.42–6.58(m, 2H), 6.69(s, 1H),<br>7.07(d, J=8.8 Hz, 1H), 8.01(s, 1H)<br>MS: 452.0[M + H]⁺<br>HPLC retention time [min.]: 4.82(method B) |
| 52 | 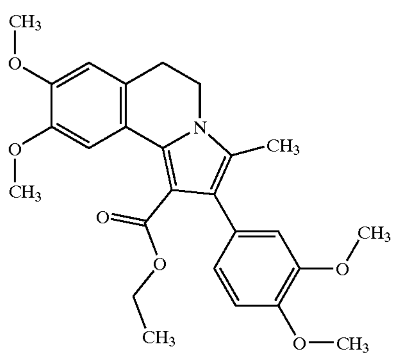 | MS: 452[M + H]⁺<br>HPLC retention time [min.]: 4.37(method D) |
| 53 | 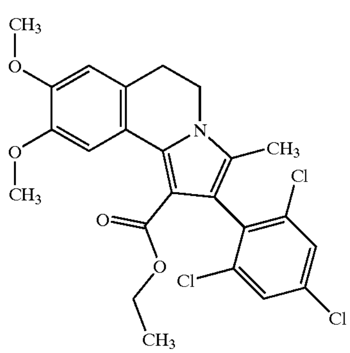 | MS: 496.1[M + H]⁺<br>HPLC retention time [min.]: 5.29(method A) |

| Ex. | Structure | Analytical data |
|---|---|---|
| 54 | 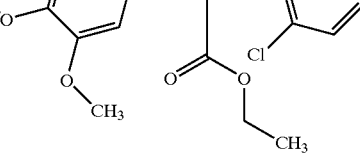 | Melting point [° C.]: 135–137 |
| 55 | 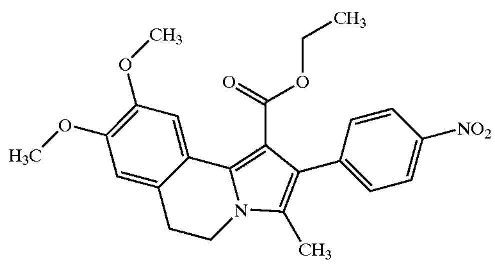 | Melting point [° C.]: 162–164 |
| 56 | 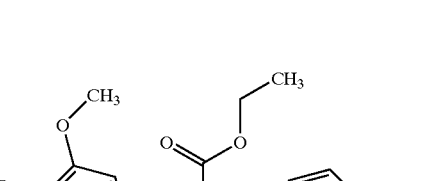 | $^1$H-NMR(400 MHz, CDCl$_3$):<br>δ = 0.92(t, J=7.2 Hz, 3H), 2.21(s, 3H),<br>2.99(t, J=6.5 Hz, 2H), 3.85(s, 6H),<br>3.86–3.98(m, 2H), 3.88(s, 3H), 3.90(s, 3H),<br>3.92(s, 3H), 4.04(q, J=7.2 Hz, 2H),<br>6.49(s, 2H), 6.72(s, 1H), 7.95(s, 1H)<br>MS: 482.4[M + H]$^+$<br>HPLC retention time [min.]: 4.43(method D) |
| 57 | 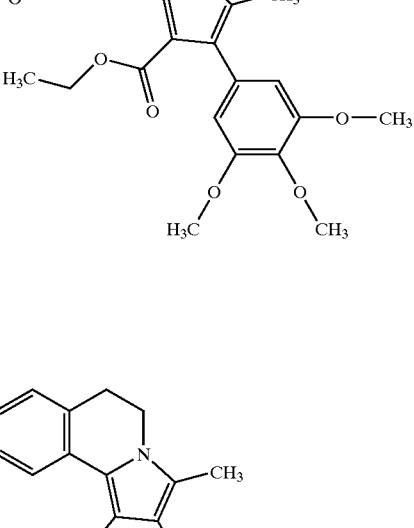 | MS: 420.3[M + H]$^+$<br>HPLC retention time [min.]: 5.24(method D) |

-continued

| Ex. | Structure | Analytical data |
|---|---|---|
| 58 | (structure) | MS: 453.3[M + H]+<br>HPLC retention time [min.]: 4.6(method A) |
| 59 | (structure) | ¹H-NMR(200 MHz, DMSO-d₆):<br>δ = 0.99(t, 3H), 2.21(s, 3H), 2.96(t, 2H),<br>3.66(s, 3H), 3.68(s, 3H), 3.75(s, 6H),<br>3.89(t, 2H), 4.00(q, 2H), 6.48(s, 2H),<br>6.93(d, 2H), 7.18(t, 1H)<br>Melting point [° C.]: 155–157 |
| 60 | (structure) | ¹H-NMR(300 MHz, CDCl₃):<br>δ = 1.08(t, 3H), 2.21(s, 3H), 3.02(t, 2H),<br>3.77(s, 3H), 3.84(s, 3H), 3.88(t, 2H), 4.11(q, 2H),<br>6.40–6.45(m, 2H), 7.50(t, 1H),<br>7.66–7.71(m, 1H), 8.08–8.13(m, 1H),<br>8.19–8.22(m, 1H)<br>Melting point [° C.]: 179–180 |
| 61 | (structure) | HPLC retention time [min.]: 5.18(method E) |

-continued

| Ex. | Structure | Analytical data |
|---|---|---|
| 62 | (structure) | Melting point [° C.]: 187–188 |
| 63 | (structure) | MS: 442.0[M + H]+<br>HPLC retention time [min.]: 5.52(method B) |
| 64 | (structure) | $^1$H NMR(300 MHz, DMSO-d$_6$):<br>δ = 0.89(t, J=7.0 Hz, 3H), 2.14(s, 3H),<br>2.31(s, 3H), 2.95(t, J=6.4 Hz, 2H),<br>3.72(s, 3H), 3.74(s, 3H), 3.79(s, 3H),<br>3.88–4.01(m, 4H), 5.04(s, 2H),<br>6.66(dd, J=8.1 Hz, J=2.1 Hz, 1H),<br>6.76(d, J=1.9 Hz, 1H), 6.94(s, 1H),<br>7.00(d, J=8.3 Hz, 1H), 7.20(d, J=8.0 Hz, 2H),<br>7.34(d, J=8.0 Hz, 2H), 7.63(s, 1H)<br>MS: 542.3[M + H]+<br>HPLC retention time [min.]: 5.09(method A) |
| 65 | (structure) | MS: 558.3[M + H]+<br>HPLC retention time [min.]: 4.85(method A) |

-continued
| Ex. | Structure | Analytical data |
|---|---|---|
| 66 | 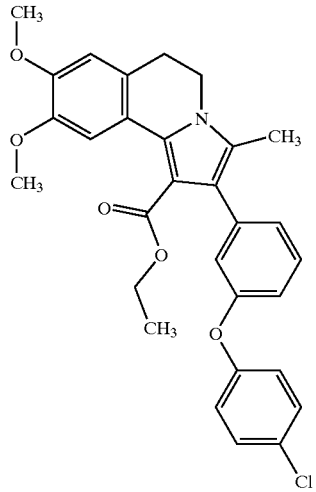 | MS: 518.2[M + H]+<br>HPLC retention time [min.]: 5.4(method A) |
| 67 | 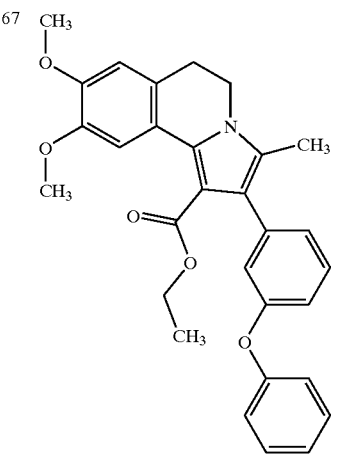 | MS: 484.3[M + H]+<br>HPLC retention time [min.]: 5.3(method D) |
| 68 | 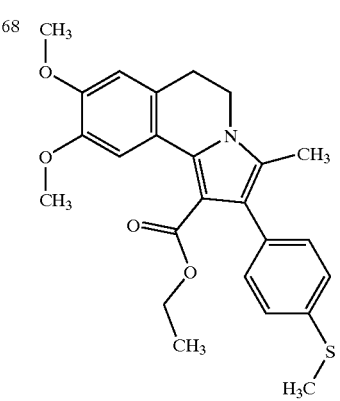 | MS: 438.3[M + H]+<br>HPLC retention time [min.]: 4.98(method D) |

| Ex. | Structure | Analytical data |
|---|---|---|
| 69 | 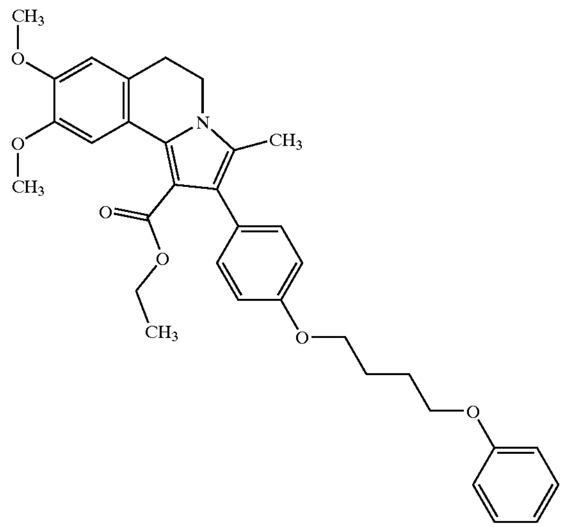 | MS: 556.3[M + H]+<br>HPLC retention time [min.]: 5.37(method A) |
| 70 | 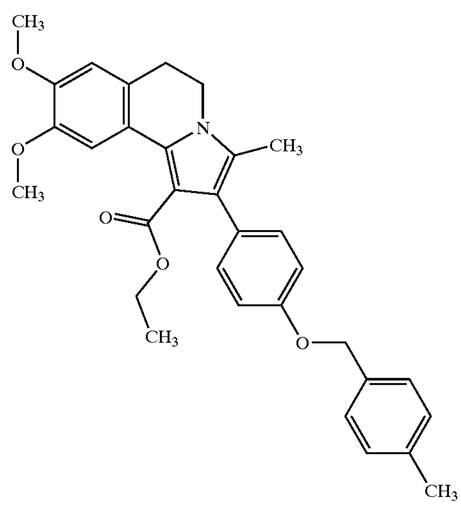 | 1H NMR(300 MHz, DMSO-d6):<br>δ = 0.19(t, J=7.0 Hz, 3H), 2.20–2.40(m, 2H),<br>2.44–2.66(m, 1H), 2.69–2.83(m, 1H),<br>3.02(t, J=6.2 Hz, 2H), 3.39(s, 3H),<br>3.44–3.60(m, 2H), 3.72(s, 3H), 3.81(s, 3H),<br>3.96–4.16(m, 2H), 6.99(s, 1H), 7.26–<br>7.62(m, 5H), 7.83–7.96(m, 3H)<br>MS: 514.4[M + H]+, 531.4[M + NH4]+<br>HPLC retention time [min.]: 5.22(method B) |
| 71 | 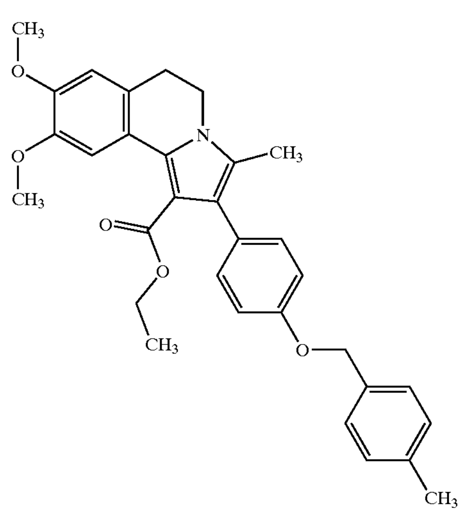 | 1H NMR(200 MHz, DMSO-d6):<br>δ = 0.87(t, J=7.1 Hz, 3H), 2.11(s, 3H),<br>2.31(s, 3H), 2.87–3.04(m, 2H), 3.71(s, 3H),<br>3.79(s, 3H), 3.84–4.04(m, 4H), 5.06(s, 2H),<br>6.90–7.12(m, 5H), 7.20(d, J=7.7 Hz, 2H),<br>7.35(d, J=7.8 Hz, 2H), 7.63(s, 1H)<br>MS: 512.3[M + H]+<br>HPLC retention time [min.]: 5.28(method A) |

-continued

| Ex. | Structure | Analytical data |
|---|---|---|
| 72 | (structure) | MS: 514.2[M + H]+<br>HPLC retention time [min.]: 5.17(method A) |
| 73 | (structure) | MS: 514.4[M + H]+, 528.3[M + NH4]+<br>HPLC retention time [min.]: 5.04(method D) |
| 74 | (structure) | MS: 498.3[M + H]+<br>HPLC retention time [min.]: 5.23(method D) |

-continued
| Ex. | Structure | Analytical data |
|---|---|---|
| 75 | 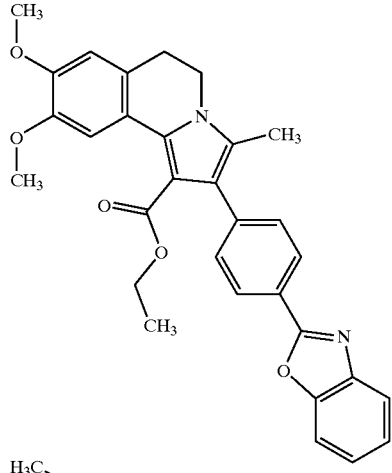 | MS: 509.3[M + H]+<br>HPLC retention time [min.]: 5.25(method D) |
| 76 | 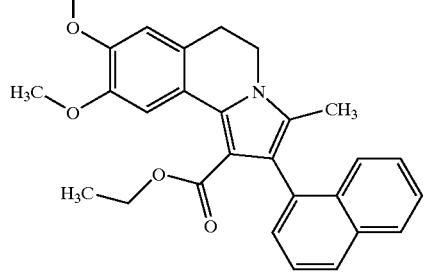 | Melting point [° C.]: 170–171 |
| 77 | 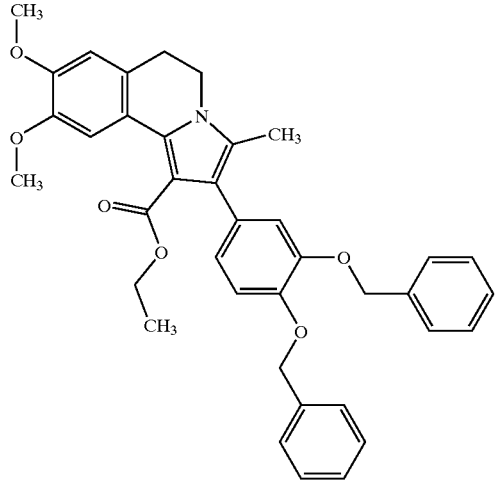 | MS: 604.3[M + H]+<br>HPLC retention time [min.]: 5.29(method A) |
| 78 | 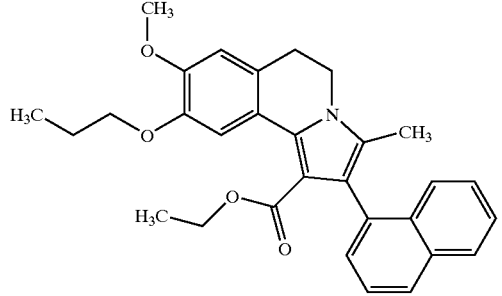 | Melting point [° C.]: 136–137 |

-continued

| Ex. | Structure | Analytical data |
|---|---|---|
| 79 | 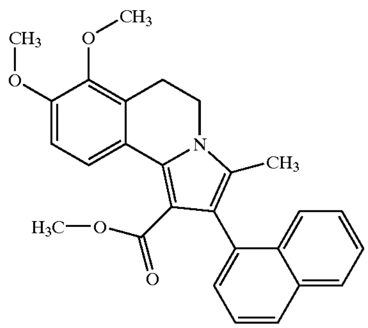 | Melting point [° C.]: 170 |
| 80 | 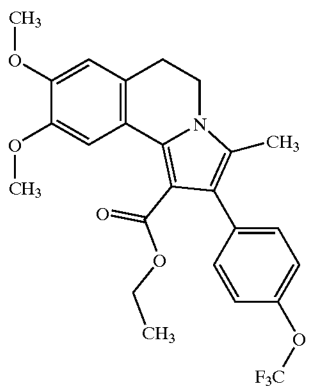 | MS: 476.2[M + H]+<br>HPLC retention time [min.]: 5.12(method A) |
| 81 | 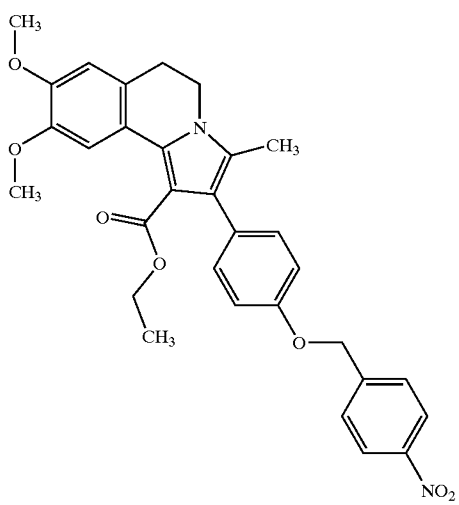 | MS: 543.3[M + H]+<br>HPLC retention time [min.]: 4.99(method A) |
| 82 | 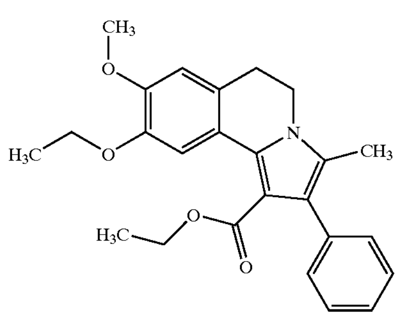 | Melting point [° C.]: 128–129 |

-continued
| Ex. | Structure | Analytical data |
|---|---|---|
| 83 | 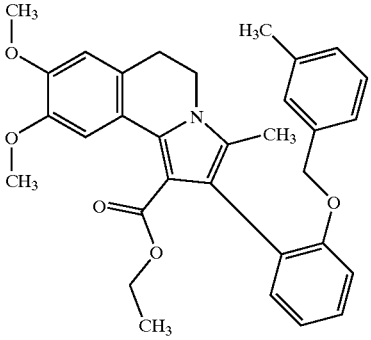 | MS: 512.3[M + H]⁺<br>HPLC retention time [min.]: 5.18(method A) |
| 84 | 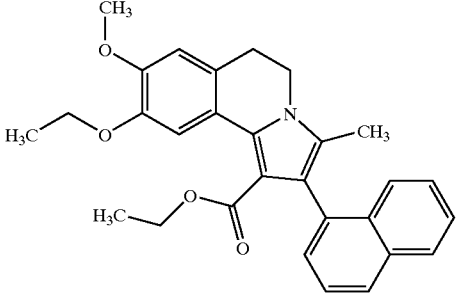 | Melting point [° C.]: 178–179 |
| 85 | 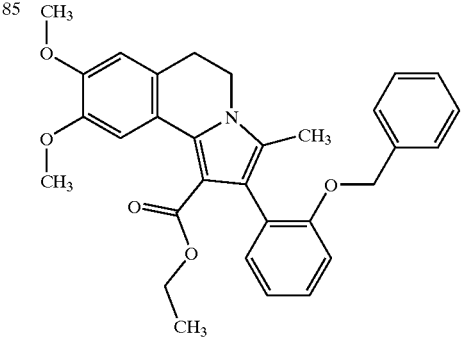 | MS: 498.3[M + H]⁺<br>HPLC retention time [min.]: 5.03(method A) |
| 86 | 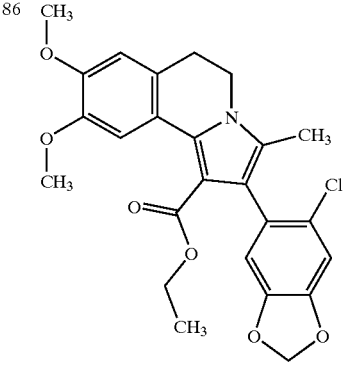 | MS: 470.3[M + H]⁺<br>HPLC retention time [min.]: 4.76(method D) |

| Ex. | Structure | Analytical data |
|---|---|---|
| 87 | (structure) | MS: 498.3[M + H]⁺<br>HPLC retention time [min.]: 5.23(method D) |
| 88 | (structure) | ¹H NMR(200 MHz, DMSO-d₆):<br>δ = 0.14(t, J=7.2 Hz, 3H), 2.05(s, 3H),<br>3.04(t, J=6.3 Hz, 2H), 3.54(q, J=7.1 Hz, 2H),<br>3.74(s, 3H), 3.82(s, 3H), 4.05(t, J=6.3 Hz, 2H),<br>6.99(s, 1H), 7.43–7.79(m, 6H), 7.88–8.07(m, 2H),<br>8.73–8.99(m, 2H)<br>MS: 492.4[M + H]⁺, 511.0[M + NH₄]⁺<br>HPLC retention time [min.]: 5.86(method B) |
| 89 | (structure) | |
| 90 | (structure) | MS: 450.3[M + H]⁺<br>HPLC retention time [min.]: 4.57(method D) |

Example 91

Ethyl 8,9dimethoxy-3-methyl-2-(3-pyrrolidinyl-phenyl)-5,6-dihydro-pyrrolo[2,1-a]-isoquinoline-1-carboxylate Following the procedure described in Example 1, ethyl (6,7-dimethoxy-3,4-dihydro-1(2H)-isoquinolinylidene)-ethanoate (Example III.1), 3-nitro-benzaldehyde, and nitroethane were reacted to give ethyl 8,9-dimethoxy-3-methyl-2-(3-nitrophenyl)-5,6-dihydro-pyrrolo[2,1-a]-isoquinoline-1-carboxylate.

4.5 g (10.31 mmol) of this compound were dissolved in 500 mL of warm methanol, 2.03 g of 10% strength palladium on charcoal were added, and the compound was hydrogenated at atmospheric pressure. The reaction mixture was filtered through a filter aid, the filtrate was evaporated under reduced pressure to a volume of approx. 150 mL, and the resulting precipitate was filtered off to give 3.36 g (80.2%) of ethyl 2-(3-aminophenyl)-8,9-dimethoxy-3-methyl-5,6-dihydropyrrolo[2,1-a]-isoquinoline-1-carboxylate.

168.5 mg (1.11 mmol) of DBU and 79.9 mg (0.37 mmol) of 1,4-dibromobutane were added to a solution of 150 mg (0.37 mmol) of ethyl 2-(3-aminophenyl)-8,9-dimethoxy-3-methyl-5,6-dihydropyrrolo[2,1-a]isoquinoline-1-carboxylate obtained as described above in 3 mL of DMF. The mixture was stirred at 120° C. for 20 hours, the solvent was evaporated under reduced pressure, and the residue was taken up in an ethyl acetate/water mixture. The layers were separated, the aqueous layer was extracted with ethyl acetate, and the combined organic phases were washed with water, dried over $Na_2SO_4$ and the solvent was evaporated under reduced pressure. Chromatography on a short silica gel column using a dichloromethane/ethyl acetate 10:1 mixture as eluant, followed by crystallization from diethyl ether gave the title compound.

$^1$H-NMR (200 MHz, $CDCl_3$):

δ=0.94 (t, 3H), 1.93–2.09 (m, 4H), 2.22 (s, 3H), 2.99 (t, 2H), 3.23–3.39 (m, 4H), 3.90 (s, 3H), 3.91 (s, 3H), 3.93 (t, 2H), 4.05 (q, 2H), 6.43–6.64 (m, 3H), 6.71 (s, 1H), 7.15–7.24 (m, 1H), 7.90 (s, 1H).

Melting point [° C.]: 141–142

We claim:

1. A compound of the formula (I)

(I)

wherein x and y independently from each other denote zero or 1 with the proviso that x+y=1 or 2;

$R^1$ and $R^2$ independently from each other denote hydrogen, $C_{1-4}$-alkyl or $CF_3$ or $R^1$ and $R^2$ together form a $C_{1-4}$-alkylene bridge;

$R^3$ and $R^4$ independently from each other denote $C_{1-4}$-alkyl;

$R^5$ denotes $C_{6-14}$-aryl, optionally having 1 to 3 further substituents selected from the group consisting of
halogen;
$C_{1-6}$-alkyl which can be further substituted with one or more radicals selected from the group consisting of OH, halogen, $NH_2$ and $C_{1-6}$-alkoxy;
$C_{1-6}$alkoxy which can be further substituted with one or more radicals selected from the group consisting of OH, halogen, $NH_2$, $C_{1-6}$-alkoxy and $C_{6-10}$-aryloxy;
OH;
$NO_2$;
CN;
$CF_3$;
$OCF_3$;
$NR^6R^7$;
$SR^8$;
—O—$(CH_2)_{1-4}$—O— wherein the oxygen atoms are bound to the aryl moiety in ortho-position to each other;
phenyloxy or benzyloxy wherein the phenyl moieties optionally contain one further substituent selected from the group consisting of $C_{1-6}$-alkyl, $C_{1-6}$-alkoxy, halogen, and $NO_2$;
phenyl, optionally substituted with CN; and
4- to 9-membered heterocyclyl containing 1 to 4 hetero atoms selected from the group consisting of N, O, and S;

$R^6$ and $R^7$ independently from each other denote hydrogen, $C_{1-6}$-alkyl or, together with the nitrogen atom to which they are attached, form a 5- to 7-membered saturated, partially unsaturated or aromatic ring which can contain up to 3 further hetero atoms selected from the group consisting of N, O, and S, and which ring can contain 1 to 3 substituents selected from the group consisting of $C_{1-6}$-alkyl, $C_{1-6}$-alkoxy, $C_{6-10}$-aryl and 4 to 9-membered aromatic heterocyclyl containing 1 to 4 hetero atoms selected from the group consisting of N, O, and S; and $R^8$ denotes hydrogen, $C_{1-6}$-alkyl or $C_{6-10}$-aryl-$C_{1-6}$-alkyl with the proviso that 8,9-dimethoxy-3-methyl-2-phenyl-5,6-dihydro-pyrrolo-[2.1-a]isoquinoline-1-carboxylic acid ethyl ester is excluded, or an isomer, a pharmaceutically acceptable salt, a hydrate or a hydrate of a pharmaceutically acceptable salt thereof.

2. A compound of formula (I) according to claim 1, wherein x and y independently from each other denote zero or 1 with the proviso that x+y=1 or 2;

$R^1$ and $R^2$ independently from each other denote hydrogen, $C_{1-4}$-alkyl or $CF_3$ or $R^1$ and $R^2$ together form a $C_{1-4}$-alkylene bridge;

$R^3$ and $R^4$ independently from each other denote $C_{1-4}$-alkyl;

$R^5$ denotes (i) phenyl, optionally having 1 to 3 further substituents selected from the group consisting of F, Cl, Br;
$C_{1-6}$-alkyl;
$C_{1-6}$-alkoxy;
$C_{6-10}$-aryloxy-$C_{1-6}$-alkoxy;
OH;
$NO_2$;
CN;
$CF_3$;
$OCF_3$;
$NR^6R^7$;
$SR^8$;
—O—$(CH_2)_{2-3}$—O— wherein the oxygen atoms are bound to the phenyl moiety in ortho-position to each other;
phenyloxy or benzyloxy wherein the phenyl moieties optionally contain one further substituent selected from the group consisting of $C_{1-6}$-alkyl, $C_{1-6}$-alkoxy, F, Cl, Br, and $NO_2$;
phenyl, optionally substituted with CN; and
benzoxazolyl;

(ii) napthyl, optionally having 1 to 3 further substituents selected from the group consisting of F, Cl, Br;
$C_{1-6}$-alkyl;
$C_{1-6}$-alkoxy;
$CF_3$; and
$NR^6R^7$ (wherein $R^6$ and $R^7$ are as defined above); or (iii) phenanthrenyl;

$R^6$ and $R^7$ independently from each other denote hydrogen, $C_{1-6}$-alkyl or, together with the nitrogen atom to which they are attached, form a 5- to 7-membered saturated heterocyclyl which can contain up to 3 further hetero atoms selected from the group consisting of N, O, and S, and which saturated heterocyclyl can contain 1 to 3 substituents selected from the group consisting of $C_{1-6}$-alkyl, $C_{1-6}$-alkoxy, $C_{6-10}$-aryl and 4- to 9-membered aromatic heterocyclyl containing 1 to 4 hetero atoms selected from the group consisting of N, O, and S; and $R^8$ denotes hydrogen, $C_{1-6}$-alkyl or $C_{6-10}$-aryl-$C_{1-6}$-alkyl with the proviso that 8,9-dimethoxy-3-methyl-2-phenyl-5,6-dihydro-pyrrolo-[2.1-a]isoquinoline-1-carboxylic acid ethyl ester is excluded, or an isomer, a pharmaceutically acceptable salt, a hydrate or a hydrate of a pharmaceutically acceptable salt thereof.

3. A compound of formula (I) according to claim 1, wherein x and y independently from each other denote zero or 1 with the proviso that x+y=1 or 2;

$R^1$ and $R^2$ independently from each other denote hydrogen, $C_{1-4}$-alkyl or $CF_3$ or $R^{1\ and\ R2}$ together form a methylene bridge;

$R^3$ and $R^4$ independently from each other denote $C_{1-4}$-alkyl;

$R^5$ denotes (i) phenyl, optionally having 1 to 3 further substituents selected from the group consisting of F, Cl, Br;
$CH_3$, $C_2H_5$, i-$C_3H_7$;
$OCH_3$, $OC_2H_5$, i-$OC_3H_7$;
phenyloxy-$C_{1-4}$-alkoxy;
OH;
$NO_2$;
CN;
$CF_3$;
$OCF_3$;
$NR^6R^7$;
$SR^8$;
—O—$(CH_2)_{2-3}$—O— wherein the oxygen atoms are bound to the phenyl moiety in ortho-position to each other;
phenyloxy or benzyloxy wherein the phenyl moieties optionally contain one further substituent selected from the group consisting of $C_{1-4}$-alkyl, $C_{1-4}$-alkoxy, F, Cl, Br, and $NO_2$;
phenyl, optionally substituted with CN; and
benzoxazolyl;

(ii) napthyl, optionally having 1 to 3 further substituents selected from the group consisting of F, Cl, Br;
$C_{1-4}$-alkoxy;
$CF_3$; and
$NR^6R^7$ (wherein $R^6$ and $R^7$ are as defined above); or (iii) phenanthrenyl;

$R^6$ and $R^7$ independently from each other denote hydrogen, $C_{1-6}$-alkyl or, together with the nitrogen atom to which they are attached, form a 5- to 7-membered saturated ring; and $R^8$ denotes hydrogen, $C_{1-4}$-alkyl or phenyl-$C_{1-4}$-alkyl with the proviso that 8,9-dimethoxy-3-methyl-2-phenyl-5,6-dihydro-pyrrolo-[2.1-a]isoquinoline-1-carboxylic acid ethyl ester is excluded, an isomer, pharmaceutically acceptable salt, a hydrate or a hydrate of a pharmaceutically acceptable salt thereof.

4. A process for manufacturing a compound according to claim 1 comprising the reaction of a compound of the formula (IV)

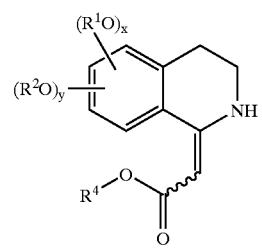

wherein x, y, $R^1$, $R^2$ and $R^4$ are as defined in claim 1, (A) with compounds of the formulae

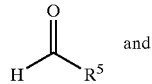 (II)

and

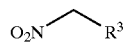 (III)

wherein $R^3$ and $R^5$ are as defined in claim 1, or (B) with a compound of the formula

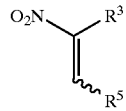 (V)

wherein $R^3$ and $R^5$ are as defined in claim 1, and optionally (C) the conversion of compound (I) obtained through either process [A] or [B] into an isomer, a (pharmaceutically acceptable) salt, a hydrate or a hydrate of a (pharmaceutically acceptable) salt thereof.

5. Method of manufacturing a pharmaceutical composition by combining one or more of the compounds according to claims 1 to 3 with one or more pharmacologically acceptable formulating agent.

6. Pharmaceutical composition comprising as an active ingredient an effective amount of one or more of the compounds according to claims 1 to 3 and one or more pharmacologically acceptable formulating agent.

7. A pharmaceutical composition in dosage unit form comprising an effective amount of a compound according to claims 1 to 3 together with an inert pharmaceutical carrier.

8. A method of treating breast cancer in a mammals comprising administering to said mammal an effective amount of one or more compound according to claims 1 to 3 either alone or in admixture with a diluent or in the form of a pharmaceutical composition.

* * * * *